(12) United States Patent
Hu et al.

(10) Patent No.: US 9,789,101 B2
(45) Date of Patent: Oct. 17, 2017

(54) METHODS AND COMPOSITIONS FOR TREATING MICROBIAL INFECTION USING PYRROLOQUINONE

(75) Inventors: Yanmin Hu, London (GB); Anthony M. R. Coates, London (GB)

(73) Assignee: HELPERBY THERAPEUTICS LIMITED, London (GB)

( * ) Notice: Subject to any disclaimer, the term of this patent is extended or adjusted under 35 U.S.C. 154(b) by 141 days.

(21) Appl. No.: 13/624,488

(22) PCT Filed: Mar. 29, 2011

(86) PCT No.: PCT/GB2011/050641
§ 371 (c)(1),
(2), (4) Date: Dec. 24, 2012

(87) PCT Pub. No.: WO2011/121345
PCT Pub. Date: Oct. 6, 2011

(65) Prior Publication Data
US 2013/0096151 A1    Apr. 18, 2013

(30) Foreign Application Priority Data

Mar. 30, 2010 (GB) .................................. 1005318.9
Aug. 5, 2010 (GB) .................................. 1013211.6

(51) Int. Cl.
| | |
|---|---|
| A61K 31/4745 | (2006.01) |
| A61K 31/4439 | (2006.01) |
| A61K 31/4453 | (2006.01) |
| A61K 31/351 | (2006.01) |
| A61K 31/445 | (2006.01) |
| A61K 31/4709 | (2006.01) |
| A61K 45/06 | (2006.01) |

(52) U.S. Cl.
CPC ........ *A61K 31/4453* (2013.01); *A61K 31/351* (2013.01); *A61K 31/445* (2013.01); *A61K 31/4439* (2013.01); *A61K 31/4709* (2013.01); *A61K 31/4745* (2013.01); *A61K 45/06* (2013.01)

(58) Field of Classification Search
None
See application file for complete search history.

(56) References Cited

U.S. PATENT DOCUMENTS

| | | | | |
|---|---|---|---|---|
| 6,565,895 B2 * | 5/2003 | Goddard et al. | ............... | 424/653 |
| 8,207,187 B2 * | 6/2012 | Beck et al. | ................... | 514/292 |

FOREIGN PATENT DOCUMENTS

WO    WO 2007/054693    *    5/2007

OTHER PUBLICATIONS

Florestano H J et al: "Antimicrobial properties of dyclonine hydrochloride, a new topical anesthetic", Journal of the American Pharmaceutical Association, Washington, DC, US, vol. 45, No. 5, May 1, 1956 (May 1, 1956), pp. 320-325.
Johnson Svena M et al: "Local anesthetics as antimicrobial agents: a review.", Surgical Infections Apr. 2008 LNKD-PUBMED: 18426354, vol. 9, No. 2, Apr. 2008 (Apr. 2008), pp. 205-213.
Kaminester et al: "A double-blind, placebo-controlled study of topical tetracaine in the treatment of herpes 1 abi ali s", Journal of the American Academy of Dermatology, C.V. Mosby, St. Louis, MO, US, vol. 41, No. 6, Dec. 1, 1999 (Dec. 1, 1999), pp. 996-1001.

* cited by examiner

*Primary Examiner* — Anna Pagonakis
(74) *Attorney, Agent, or Firm* — Steptoe & Johnson LLP

(57) ABSTRACT

A pharmaceutical composition can include dyclonine hydrochloride and 4-methyl-1-(2-phenylethyl)-8-phenoxy-2,3-dihydro-1H-pyrrolo[3,2-c]-quinoline.

4 Claims, 6 Drawing Sheets

METHODS AND COMPOSITIONS FOR TREATING MICROBIAL INFECTION USING PYRROLOQUINONE

CLAIM FOR PRIORITY

This application claims priority under 35 USC 371 to International Application No. PCT/GB2011/050641, filed on Mar. 29, 2011, which claims priority to British Applications Nos. 1005318.9, filed Mar. 30, 2010 and 1013211.6, filed Aug. 5, 2010, each of which is hereby incorporated by reference in its entirety.

TECHNICAL FIELD

The present invention relates to a pharmaceutical composition.

BACKGROUND

Patients suffering from acute microbial infections used to have a low chance of survival. Antimicrobial agent can kill microorganisms or inhibits their growth.

SUMMARY

A pharmaceutical composition can include dyclonine hydrochloride and 4-methyl-1-(2-phenylethyl)-8-phenoxy-2,3-dihydro-1 H-pyrrolo [3,2-c]-quinoline.

DETAILED DESCRIPTION

Figure 1:
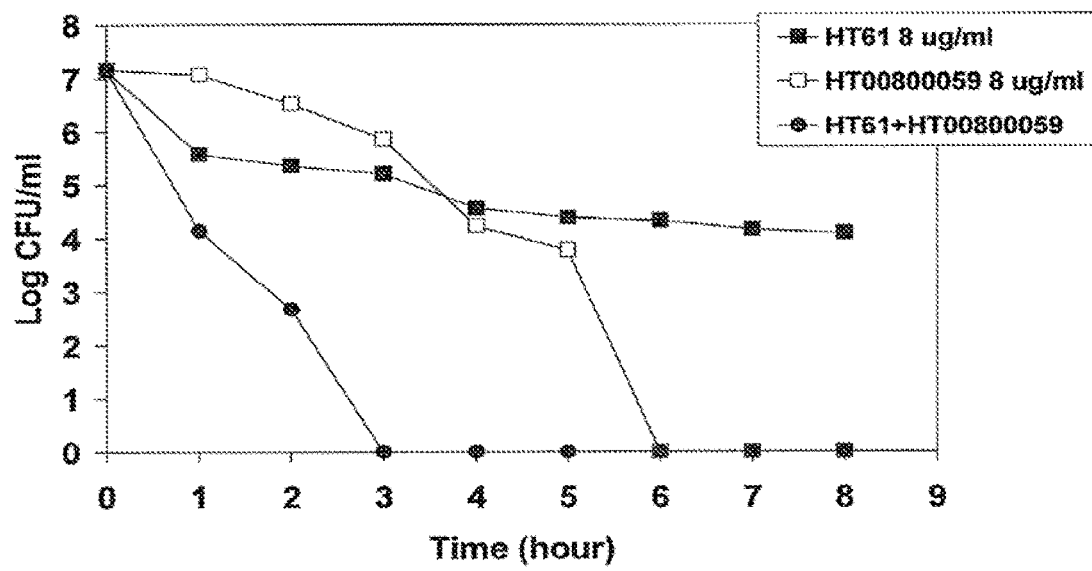
FIG. 1 shows an effect of HT61 and HT00800059 in combination against stationary phase *Staphylococcus aureus*.

The present invention relates to the use of an anesthetic agent for killing clinically latent microorganisms associated with microbial infections and to novel combinations comprising an anesthetic agent and an antimicrobial agent for the treatment of microbial infections.

Before the introduction of antibiotics, patients suffering from acute microbial infections (e.g. tuberculosis or pneumonia) had a low chance of survival. For example, mortality from tuberculosis was around 50%. Although the introduction of antimicrobial agents in the 1940s and 1950s rapidly changed this picture, bacteria have responded by progressively gaining resistance to commonly used antibiotics. Now, every country in the world has antibiotic-resistant bacteria. Indeed, more than 70% of bacteria that give rise to hospital acquired infections in the USA resist at least one of the main antimicrobial agents that are typically used to fight infection (*Nature Reviews, Drug Discovery*, 1, 895-910 (2002)).

One way of tackling the growing problem of resistant bacteria is the development of new classes of antimicrobial agents. However, until the introduction of linezolid in 2000, there had been no new class of antibiotic marketed for over 37 years. Moreover, even the development of new classes of antibiotic provides only a temporary solution, and indeed there are already reports of resistance of certain bacteria to linezolid (*Lancet*, 357, 1179 (2001) and *Lancet*, 358, 207-208 (2001)).

In order to develop more long-term solutions to the problem of bacterial resistance, it is clear that alternative approaches are required. One such alternative approach is to minimise, as much as is possible, the opportunities that bacteria are given for developing resistance to important antibiotics. Thus, strategies that can be adopted include limiting the use of antibiotics for the treatment of non-acute infections, as well as controlling which antibiotics are fed to animals in order to promote growth.

However, in order to tackle the problem more effectively, it is necessary to gain an understanding of the actual mechanisms by which bacteria generate resistance to antibiotic agents. To do this requires first a consideration of how current antibiotic agents work to kill bacteria.

Antimicrobial agents target essential components of bacterial metabolism. For example, the β-lactams (e.g. penicillins and cephalosporins) inhibit cell wall synthesis, whereas other agents inhibit a diverse range of targets, such as DNA gyrase (quinolones) and protein synthesis (e.g. macrolides, aminoglycosides, tetracyclines and oxazolidinones). The range of organisms against which the antimicrobial agents are effective varies, depending upon which organisms are heavily reliant upon the metabolic step(s) that is/are inhibited. Further, the effect upon bacteria can vary from a mere inhibition of growth (i.e. a bacteriostatic effect, as seen with agents such as the tetracyclines) to full killing (i.e. a bactericidal effect, as seen, e.g. with penicillin).

Bacteria have been growing on Earth for more than 3 billion years and, in that time, have needed to respond to vast numbers of environmental stresses. It is therefore perhaps not surprising that bacteria have developed a seemingly inexhaustible variety of mechanisms by which they can respond to the metabolic stresses imposed upon them by antibiotic agents. Indeed, mechanisms by which the bacteria can generate resistance include strategies as diverse as inactivation of the drug, modification of the site of action, modification of the permeability of the cell wall, overproduction of the target enzyme and bypass of the inhibited steps. Nevertheless, the rate of resistance emerges to a particular agent has been observed to vary widely, depending upon factors such as the agent's mechanism of action, whether the agent's mode of killing is time- or concentration-dependent, the potency against the population of bacteria and the magnitude and duration of the available serum concentration.

It has been proposed (*Science*, 264, 388-393 (1994)) that agents that target single enzymes (e.g. rifampicin) are the most prone to the development of resistance. Further, the longer that suboptimal levels of antimicrobial agent are in contact with the bacteria, the more likely the emergence of resistance.

Moreover, it is now known that many microbial infections include sub-populations of bacteria that are phenotypically resistant to antimicrobials (*J. Antimicrob. Chemother.*, 4, 395-404 (1988); *J. Med. Microbiol.*, 38, 197-202 (1993); *J. Bacteriol.*, 182, 1794-1801 (2000); ibid. 182, 6358-6365 (2000); ibid. 183, 6746-6751 (2001); *FEMS Microbiol. Lett.*, 202, 59-65 (2001); and *Trends in Microbiology*, 13, 34-40 (2005)). There appear to be several types of such phenotypically resistant bacteria, including persisters, stationary-phase bacteria, as well as those in the depths of biofilms. However, each of these types is characterised by its low rate of growth compared to log-phase bacteria under the same conditions. Nutritional starvation and high cell densities are also common characteristics of such bacteria.

Although resistant to antimicrobial agents in their slow-growing state, phenotypically resistant bacteria differ from those that are genotypically resistant in that they regain their susceptibility to antimicrobials when they return to a fast-growing state (e.g. when nutrients become more readily available to them).

The presence of phenotypically resistant bacteria in an infection leads to the need for prolonged courses of antimicrobial agents, comprising multiple doses. This is because the resistant, slowly multiplying bacteria provide a pool of "latent" organisms that can convert to a fast-growing state when the conditions allow (thereby effectively re-initiating the infection). Multiple doses over time deal with this issue by gradually killing off the "latent" bacteria that convert to "active" form.

However, dealing with "latent" bacteria by administering prolonged courses of antimicrobials poses its own problems. That is, prolonged exposure of bacteria to suboptimal concentrations of antimicrobial agent can lead to the emergence of genotypically resistant bacteria, which can then multiply rapidly in the presence of even high concentrations of the antimicrobial.

Long courses of antimicrobials are more likely to encourage the emergence of genotypic resistance than shorter courses on the grounds that non-multiplying bacterial will tend to survive and, interestingly, probably have an enhanced ability to mutate to resistance (*Proc. Natl. Acad. Sci. USA*, 92, 11736-11740 (1995); *J. Bacteriol.*, 179, 6688-6691 (1997); and *Antimicrob. Agents Chemother.*, 44, 1771-1777 (2000)).

In the light of the above, a new approach to combating the problem of bacterial resistance might be to select and develop antimicrobial agents on the basis of their ability to kill "latent" microorganisms. The production of such agents would allow, amongst other things, for the shortening of chemotherapy regimes in the treatment of microbial infections, thus reducing the frequency with which genotypical resistance arises in microorganisms.

International Patent Application, Publication Number WO2000028074 describes a method of screening compounds to determine their ability to kill clinically latent microorganisms. Using this method, the Applicant has observed that many conventional antimicrobial agents, such as augmentin, azithromycin, levofloxacin, linezolid and mupirocin, which otherwise exhibit excellent biological activity against log phase (i.e. multiplying) bacteria, exhibit little or no activity against clinically latent microorganisms. This observation has necessitated the development of novel antimicrobials which may be used to kill clinically latent microorganisms.

International Patent Application, Publication Numbers WO2007054693, WO2008117079 and WO2008142384 describe compounds which exhibit biological activity against clinically latent microorganisms. Examples of such compounds include 4-methyl-1-(2-phenylethyl)-8-phenoxy-2,3-dihydro-1H-pyrrolo[3,2-c]-quinoline, 4-(3-benzylpyrrolidin-1-yl)-2-methyl-6-phenoxyquinoline, N-[4-(3-benzylpyrrolidin-1-yl)-2-methylquinolin-6-yl]benzamide and pharmaceutically acceptable derivatives thereof.

A wide variety of both general and local anesthetic agents are known and commercially available. Local anesthetics initiate their analgesic activities by reversibly blocking neural voltage-gated $Na^+$ channels in the cell membrane and thus preventing $Na^+$ influxes. This subsequently prevents the production of action potentials and nerve conduction. It is these mechanisms of action that may allow local anesthetics to influence a wide range of tissues thereby reducing inflammation.

In addition to analgesic activity, certain local anesthetics have also been shown to possess antimicrobial activity. Limited studies attribute the mechanism of action of antimicrobial activity of local anesthetics to a disruption of microbial cell membrane permeability, leading to leakage of cellular components and subsequent cell lysis (*Surg. Infect. (Larchmt).*, 9(2), 205-213, (2008)).

An example of a local anesthetic that has been shown to possess antimicrobial activity is dyclonine hydrochloride (*Journal of the American Pharmaceutical Association*, Vol. XLV, No. 5, 320-324 (1956)). Dyclonine hydrochloride was shown to exhibit activity in vitro against a variety of log phase (i.e. multiplying) bacteria. In addition, preparations containing a combination of dyclonine hydrochloride with chlorobutanol exhibited a synergistic antimicrobial effect in vitro against log phase *Staphylococcus Aureus* and *Escherichia coli* (ibid.).

However, to our knowledge, the antimicrobial effect of anesthetic agents such as dyclonine hydrochloride against clinically latent microorganisms has not been reported to date.

Accordingly, in one embodiment of the present invention there is provided the use of an anesthetic agent or a pharmaceutically acceptable derivative thereof for killing clinically latent microorganisms associated with a microbial infection. The anesthetic agent may be a general or local anesthetic, and is preferably a local anesthetic.

In another embodiment of the invention there is provided a method of killing clinically latent microorganisms associated with a microbial infection which comprises administering to a mammal, including man, an anesthetic agent or a pharmaceutically acceptable derivative thereof.

In another embodiment of the invention there is provided the use of an anesthetic agent or a pharmaceutically acceptable derivative thereof in the manufacture of a medicament for killing clinically latent microorganisms associated with a microbial infection.

In a further embodiment of the invention there is provided a pharmaceutical composition comprising an anesthetic agent and a pharmaceutically acceptable carrier for use in killing clinically latent microorganisms associated with a microbial infection.

The present invention is also based upon the unexpected finding that the activity of certain antimicrobial agents is substantially improved if such agents are administered in combination with an anesthetic agent, particularly a local anesthetic agent. Moreover, combinations of certain agents have surprisingly been shown to exhibit synergistic antimicrobial activity against log phase (i.e. multiplying) and/or clinically latent microorganisms. The surprising biological activity of the combinations of the present invention offers the opportunity to shorten chemotherapy regimes and may result in a reduction in the emergence of microbial resistance associated with the use of such combinations.

Thus, in one embodiment the present invention provides a combination comprising an antimicrobial agent or a pharmaceutically acceptable derivative thereof and an anesthetic agent or a pharmaceutically acceptable derivative thereof for use in killing clinically latent microorganisms associated with a microbial infection.

In another embodiment, the invention provides the use of an antimicrobial agent or a pharmaceutically acceptable derivative thereof in combination with an anesthetic agent or a pharmaceutically acceptable derivative thereof for the manufacture of a medicament for killing clinically latent microorganisms associated with a microbial infection.

In a further embodiment, the invention provides a method of killing clinically latent microorganisms associated with a microbial infection which comprises administering to a mammal, including man, an antimicrobial agent or a pharmaceutically acceptable derivative thereof in combination with an anesthetic agent or a pharmaceutically acceptable derivative thereof.

In still a further embodiment, the invention provides the use of an antimicrobial agent or a pharmaceutically acceptable derivative thereof in combination with an anesthetic agent or a pharmaceutically acceptable derivative thereof for killing clinically latent microorganisms associated with a microbial infection.

As used herein, the term "in combination with" covers both separate and sequential administration of an antimicrobial agent and an anesthetic agent. When the agents are administered sequentially, either the antimicrobial agent or the anesthetic agent may be administered first. When administration is simultaneous, the agents may be administered either in the same or a different pharmaceutical composition. Adjunctive therapy, i.e. where one agent is used as a primary treatment and the other agent is used to assist that primary treatment, is also an embodiment of the present invention.

According to a further embodiment of the invention, there is provided a product comprising an antimicrobial agent and an anesthetic agent as a combined preparation for simultaneous, separate or sequential use in killing clinically latent microorganisms associated with a microbial infection.

There is also provided a pharmaceutical composition comprising an antimicrobial agent, an anesthetic agent and a pharmaceutically acceptable adjuvant, diluent or carrier. Such a composition may be used for the treatment of microbial infections, in particular for use in killing clinically latent microorganisms associated with such infections.

The combinations of the present invention may be used to treat microbial infections. In particular they may be used to kill multiplying and/or clinically latent microorganisms associated with microbial infections. References herein to the treatment of a microbial infection therefore include killing multiplying and/or clinically latent microorganisms associated with such infections. Preferably, the combinations of the present invention are used to kill clinically latent microorganisms associated with microbial infections.

As used herein, "kill" means a loss of viability as assessed by a lack of metabolic activity.

As used herein, "clinically latent microorganism" means a microorganism that is metabolically active but has a growth rate that is below the threshold of infectious disease expression. The threshold of infectious disease expression refers to the growth rate threshold below which symptoms of infectious disease in a host are absent.

The metabolic activity of clinically latent microorganisms can be determined by several methods known to those skilled in the art; for example, by measuring mRNA levels in the microorganisms or by determining their rate of uridine uptake. In this respect, clinically latent microorganisms, when compared to microorganisms under logarithmic growth conditions (in vitro or in vivo), possess reduced but still significant levels of:

(I) mRNA (e.g. from 0.0001 to 50%, such as from 1 to 30, 5 to 25 or 10 to 20%, of the level of mRNA); and/or (II) uridine (e.g. [$^3$H]uridine) uptake (e.g. from 0.0005 to 50%, such as from 1 to 40, 15 to 35 or 20 to 30% of the level of [$^3$H]uridine uptake).

Clinically latent microorganisms typically possess a number of identifiable characteristics. For example, they may be viable but non-culturable; i.e. they cannot typically be detected by standard culture techniques, but are detectable and quantifiable by techniques such as broth dilution counting, microscopy, or molecular techniques such as polymerase chain reaction. In addition, clinically latent microorganisms are phenotypically tolerant, and as such are sensitive (in log phase) to the biostatic effects of conventional antimicrobial agents (i.e. microorganisms for which the minimum inhibitory concentration (MIC) of a conventional antimicrobial is substantially unchanged); but possess drastically decreased susceptibility to drug-induced killing (e.g. microorganisms for which, with any given conventional antimicrobial agent, the ratio of minimum microbiocidal concentration (e.g. minimum bactericidal concentration, MBC) to MIC is 10 or more).

As used herein, the term "microorganisms" means fungi and bacteria. References herein to "microbial", "antimicrobial" and "antimicrobially" shall be interpreted accordingly. For example, the term "microbial" means fungal or bacterial, and "microbial infection" means any fungal or bacterial infection.

As used herein, the term "bacteria" (and derivatives thereof, such as "microbial infection") includes, but is not limited to, references to organisms (or infections due to organisms) of the following classes and specific types:

Gram-positive cocci, such as Staphylococci (e.g. *Staph. aureus, Staph. epidermidis, Staph. saprophyticus, Staph. auricularis, Staph. capitis capitis, Staph. c. ureolyticus, Staph. caprae, Staph. cohnii cohnii, Staph. c. urealyticus, Staph. equorum, Staph. gallinarum, Staph. haemolyticus, Staph. hominis hominis, Staph. h. novobiosepticius, Staph. hyicus, Staph. intermedius, Staph. lugdunensis, Staph. pasteuri, Staph. saccharolyticus, Staph. schleiferi schleiferi, Staph. s. coagulans, Staph. sciuri, Staph. simulans, Staph. warneri* and *Staph. xylosus*);

Streptococci (e.g. beta-haemolytic, pyogenic streptococci (such as *Strept. agalactiae, Strept. canis, Strept. dysgalactiae dysgalactiae, Strept dysgalactiae equisimilis, Strept equi equi, Strept equi zooepidemicus, Strept. iniae, Strept porcinus* and *Strept pyogenes*), microaerophilic, pyogenic streptococci (*Streptococcus "milleri"*, such as *Strept. anginosus, Strept constellatus constellatus, Strept constellatus pharyngidis* and *Strept intermedius*), oral streptococci of the "mitis" (alpha-haemolytic-*Streptococcus "viridans"*, such as *Strept. mitis, Strept. oralis, Strept. sanguinis, Strept. cristatus, Strept gordonii* and *Strept. parasanguinis*), "*salivarius*" (non-haemolytic, such as *Strept salivarius* and *Strept vestibularis*) and "mutans" (tooth-surface streptococci, such as *Strept. criceti, Strept. mutans, Strept ratti* and *Strept sobrinus*) groups, *Strept. acidominimus, Strept. bovis, Strept. faecalis, Strept. equinus, Strept. pneumoniae* and *Strept. suis*, or Streptococci alternatively classified as Group A, B, C, D, E, G, L, P, U or V *Streptococcus*);

Gram-negative cocci, such as *Neisseria gonorrhoeae, Neisseria meningitidis, Neisseria cinerea, Neisseria elongata,*

*Neisseria flavescens, Neisseria lactamica, Neisseria mucosa, Neisseria sicca, Neisseria subflava* and *Neisseria weaveri*;

Bacillaceae, such as *Bacillus anthracis, Bacillus subtilis, Bacillus thuringiensis, Bacillus stearothermophilus* and *Bacillus cereus*;

Enterobacteriaceae, such as *Escherichia coli*, *Enterobacter* (e.g. *Enterobacter aerogenes, Enterobacter agglomerans* and *Enterobacter cloacae*), *Citrobacter* (such as *Citrob. freundii* and *Citrob. divernis*), *Hafnia* (e.g. *Hafnia alvei*), *Erwinia* (e.g. *Erwinia persicinus*), *Morganella morganii*, *Salmonella* (*Salmonella enterica* and *Salmonella typhi*), *Shigella* (e.g. *Shigella dysenteriae, Shigella flexneri, Shigella boydii* and *Shigella sonnet*), *Klebsiella* (e.g. *Klebs. pneumoniae, Klebs. oxytoca, Klebs. ornitholytica, Klebs. planticola, Klebs. ozaenae, Klebs. terrigena, Klebs. granulomatis* (*Calymmatobacterium granulomatis*) and *Klebs. rhinoscleromatis*), *Proteus* (e.g. *Pr. mirabilis, Pr. rettgeri* and *Pr. vulgaris*), *Providencia* (e.g. *Providencia alcalifaciens, Providencia rettgeri* and *Providencia stuartii*), *Serratia* (e.g. *Serratia marcescens* and *Serratia liquifaciens*), and *Yersinia* (e.g. *Yersinia enterocolitica, Yersinia pestis* and *Yersinia pseudotuberculosis*);

Enterococci (e.g. *Enterococcus avium, Enterococcus casseliflavus, Enterococcus cecorum, Enterococcus dispar, Enterococcus durans, Enterococcus faecalis, Enterococcus faecium, Enterococcus flavescens, Enterococcus gallinarum, Enterococcus hirae, Enterococcus malodoratus, Enterococcus mundtii, Enterococcus pseudoavium, Enterococcus raffinosus* and *Enterococcus solitarius*);

*Helicobacter* (e.g. *Helicobacter pylori, Helicobacter cinaedi* and *Helicobacter fennelliae*);

*Acinetobacter* (e.g. *A. baumanii, A. calcoaceticus, A. haemolyticus, A. johnsonii, A. junii, A. lwoffi* and *A. radioresistens*);

*Pseudomonas* (e.g. *Ps. aeruginosa, Ps. maltophilia* (*Stenotrophomonas maltophilia*), *Ps. alcaligenes, Ps. chlororaphis, Ps. fluorescens, Ps. luteola. Ps. mendocina, Ps. monteilii, Ps. oryzihabitans, Ps. pertocinogena, Ps. pseudalcaligenes, Ps. putida* and *Ps. stutzen*);

*Bacteriodes fragilis*;

*Peptococcus* (e.g. *Peptococcus niger*);

*Peptostreptococcus*;

*Clostridium* (e.g. *C. perfringens, C. difficile, C. botulinum, C. tetani, C. absonum, C. argentinense, C. baratii, C. bifermentans, C. beijerinckii, C. butyricum, C. cadaveris, C. camis, C. celatum, C. clostridioforme, C. cochlearium, C. cocleatum, C. fallax, C. ghonii, C. glycolicum, C. haemolyticum, C. hastiforme, C. histolyticum, C. indolis, C. innocuum, C. irregulare, C. leptum, C. limosum, C. malenominatum, C. novyi, C. oroticum, C. paraputrificum, C. piliforme, C. putrefasciens, C. ramosum, C. septicum, C. sordelii, C. sphenoides, C. sporogenes, C. subterminale, C. symbiosum* and *C. tedium*);

*Mycoplasma* (e.g. *M. pneumoniae, M. hominis, M. genitalium* and *M. urealyticum*);

Mycobacteria (e.g. *Mycobacterium tuberculosis, Mycobacterium avium, Mycobacterium fortuitum, Mycobacterium marinum, Mycobacterium kansasii, Mycobacterium chelonae, Mycobacterium abscessus, Mycobacterium leprae, Mycobacterium smegmitis, Mycobacterium africanum, Mycobacterium alvei, Mycobacterium asiaticum, Mycobacterium aurum, Mycobacterium bohemicum, Mycobacterium bovis, Mycobacterium branderi, Mycobacterium brumae, Mycobacterium celatum, Mycobacterium chubense, Mycobacterium confluentis, Mycobacterium conspicuum, Mycobacterium cookii, Mycobacterium flavescens, Mycobacterium gadium, Mycobacterium gastri, Mycobacterium genavense, Mycobacterium gordonae, Mycobacterium goodii, Mycobacterium haemophilum, Mycobacterium hassicum, Mycobacterium intracellulare, Mycobacterium interjectum, Mycobacterium heidelberense, Mycobacterium lentiflavum, Mycobacterium malmoense, Mycobacterium microgenicum, Mycobacterium microti, Mycobacterium mucogenicum, Mycobacterium neoaurum, Mycobacterium nonchromogenicum, Mycobacterium peregrinum, Mycobacterium phlei, Mycobacterium scrofulaceum, Mycobacterium shimoidei, Mycobacterium simiae, Mycobacterium szulgai, Mycobacterium terrae, Mycobacterium thermoresistabile, Mycobacterium triplex, Mycobacterium triviale, Mycobacterium tusciae, Mycobacterium ulcerans, Mycobacterium vaccae, Mycobacterium wolinskyi* and *Mycobacterium xenopi*);

*Haemophilus* (e.g. *Haemophilus influenzae, Haemophilus ducreyi, Haemophilus aegyptius, Haemophilus parainfluenzae, Haemophilus haemolyticus* and *Haemophilus parahaemolyticus*);

*Actinobacillus* (e.g. *Actinobacillus actinomycetemcomitans, Actinobacillus equuli, Actinobacillus hominis, Actinobacillus lignieresii, Actinobacillus suis* and *Actinobacillus ureae*);

*Actinomyces* (e.g. *Actinomyces israelii*);

*Brucella* (e.g. *Brucella abortus, Brucella canis, Brucella melintensis* and *Brucella suis*);

*Campylobacter* (e.g. *Campylobacter jejuni, Campylobacter coli, Campylobacter lari* and *Campylobacter fetus*);

*Listeria monocytogenes*;

*Vibrio* (e.g. *Vibrio cholerae* and *Vibrio parahaemolyticus, Vibrio alginolyticus, Vibrio carchariae, Vibrio fluvialis, Vibrio furnissii, Vibrio hollisae, Vibrio metschnikovii, Vibrio mimicus* and *Vibrio vulnificus*);

*Erysipelothrix rhusopathiae*;

Corynebacteriaceae (e.g. *Corynebacterium diphtheriae, Corynebacterium jeikeum* and *Corynebacterium urealyticum*);

Spirochaetaceae, such as *Borrelia* (e.g. *Borrelia recurrentis, Borrelia burgdorferi, Borrelia afzelii, Borrelia andersonii, Borrelia bissettii, Borrelia garinii, Borrelia japonica, Borrelia lusitaniae, Borrelia tanukii, Borrelia turdi, Borrelia valaisiana, Borrelia caucasica, Borrelia crocidurae, Borrelia duttoni, Borrelia graingeri, Borrelia hermsii, Borrelia hispanica, Borrelia latyschewii, Borrelia mazzottii, Borrelia parkeri, Borrelia persica, Borrelia turicatae* and *Borrelia venezuelensis*) and *Treponema* (*Treponema pallidum* ssp. *pallidum, Treponema pallidum* ssp. *endemicum, Treponema pallidum* ssp. *pertenue* and *Treponema carateum*);

*Pasteurella* (e.g. *Pasteurella aerogenes, Pasteurella bettyae, Pasteurella canis, Pasteurella dagmatis, Pasteurella gallinarum, Pasteurella haemolytica, Pasteurella multocida multocida, Pasteurella multocida gallicida, Pasteurella multocida septica, Pasteurella pneumotropica* and *Pasteurella stomatis*);

*Bordetella* (e.g. *Bordetella bronchiseptica, Bordetella hinzii, Bordetella holmseii, Bordetella parapertussis, Bordetella pertussis* and *Bordetella trematum*);

Nocardiaceae, such as *Nocardia* (e.g. *Nocardia asteroides* and *Nocardia brasiliensis*);

*Rickettsia* (e.g. *Ricksettsii* or *Coxiella burnetii*);

*Legionella* (e.g. *Legionalla anisa, Legionalla birminghamensis, Legionalla bozemanii, Legionalla cincinnatiensis, Legionalla dumoffii, Legionalla feeleii, Legionalla gormanii, Legionalla hackeliae, Legionalla israelensis,*

*Legionalla jordanis, Legionalla lansingensis, Legionalla longbeachae, Legionalla maceachemii, Legionalla micdadei, Legionalla oakridgensis, Legionalla pneumophila, Legionalla sainthelensi, Legionalla tucsonensis* and *Legionalla wadsworthii*);

*Moraxella catarrhalis;*

*Cyclospora cayetanensis;*

*Entamoeba histolytica;*

*Giardia lamblia;*

*Trichomonas vaginalis;*

*Toxoplasma gondii;*

*Stenotrophomonas maltophilia;*

*Burkholderia cepacia; Burkholderia mallei* and *Burkholderia pseudomallei;*

*Francisella tularensis;*

*Gardnerella* (e.g. *Gardnerella vaginalis* and *Gardneralla mobiluncus*);

*Streptobacillus moniliformis;*

Flavobacteriaceae, such as *Capnocytophaga* (e.g. *Capnocytophaga canimorsus, Capnocytophaga cynodegmi, Capnocytophaga gingivalis, Capnocytophaga granulosa, Capnocytophaga haemolytica, Capnocytophaga ochracea* and *Capnocytophaga sputigena*);

*Bartonella* (*Bartonella bacilliformis, Bartonella clarridgeiae, Bartonella elizabethae, Bartonella henselae, Bartonella quintana* and *Bartonella vinsonii arupensis*);

*Leptospira* (e.g. *Leptospira biflexa, Leptospira borgpetersenii, Leptospira inadai, Leptospira interrogans, Leptospira kirschneri, Leptospira noguchii, Leptospira santarosai* and *Leptospira weilii*);

*Spirillium* (e.g. *Spirillum minus*);

*Baceteroides* (e.g. *Bacteroides caccae, Bacteroides capillosus, Bacteroides coagulans, Bacteroides distasonis, Bacteroides eggerthii, Bacteroides forsythus, Bacteroides fragilis, Bacteroides merdae, Bacteroides ovatus, Bacteroides putredinis, Bacteroides pyogenes, Bacteroides splanchinicus, Bacteroides stercoris, Bacteroides tectus, Bacteroides thetaiotaomicron, Bacteroides uniformis, Bacteroides ureolyticus* and *Bacteroides vulgatus*);

*Prevotella* (e.g. *Prevotella bivia, Prevotella buccae, Prevotella corporis, Prevotella dentalis* (*Mitsuokefla dentalis*), *Prevotella denticola, Prevotella disiens, Prevotella enoeca, Prevotella heparinolytica, Prevotella intermedia, Prevotella loeschii, Prevotella melaminogenica, Prevotella nigrescens, Prevotella oralis, Prevotella oris, Prevotella oulora, Prevotella tannerae, Prevotella venoralis* and *Prevotella zoogleoformans*);

*Porphyromonas* (e.g. *Porphyromonas asaccharolytica, Porphyromonas cangingivalis, Porphyromonas canoris, Porphyromonas cansulci, Porphyromonas catoniae, Porphyromonas circumdentaria, Porphyromonas crevioricanis, Porphyromonas endodontalis, Porphyromonas gingivalis, Porphyromonas gingivicanis, Porphyromonas levii* and *Porphyromonas macacae*);

*Fusobacterium* (e.g. *F. gonadiaformans, F. mortiferum, F. naviforme, F. necrogenes, F. necrophorum necrophorum, F. necrophorum fundiliforme, F. nucleatum nucleatum, F. nucleatum fusiforme, F. nucleatum polymorphum, F. nucleatum vincentii, F. periodonticum, F. russii, F. ulcerans* and *F. varium*);

*Chlamydia* (e.g. *Chlamydia trachomatis*);

*Cryptosporidium* (e.g. *C. parvum, C. hominis, C. canis, C. felis, C. meleagridis* and *C. muris*);

*Chlamydophila* (e.g. *Chlamydophila abortus* (*Chlamydia psittaci*), *Chlamydophila pneumoniae* (*Chlamydia pneumoniae*) and *Chlamydophila psittaci* (*Chlamydia psittaci*));

*Leuconostoc* (e.g. *Leuconostoc citreum, Leuconostoc cremoris, Leuconostoc dextranicum, Leuconostoc lactis, Leuconostoc mesenteroides* and *Leuconostoc pseudomesenteroides*);

*Gemella* (e.g. *Gemella bergeri, Gemella haemolysans, Gemella morbillorum* and *Gemella sanguinis*); and

*Ureaplasma* (e.g. *Ureaplasma parvum* and *Ureaplasma urealyticum*).

As used herein, the term "fungi" (and derivatives thereof, such as "fungal infection") includes, but is not limited to, references to organisms (or infections due to organisms) of the following classes and specific types:

*Absidia* (e.g. *Absidia corymbifera*);

*Ajellomyces* (e.g. *Ajellomyces capsulatus* and *Ajellomyces dermatitidis*);

*Arthroderma* (e.g. *Arthroderma benhamiae, Arthroderma fulvum, Arthroderma gypseum, Arthroderma incurvatum, Arthroderma otae* and *Arthroderma vanbreuseghemii*);

*Aspergillus* (e.g. *Aspergillus flavus, Aspergillus fumigatus* and *Aspergillus niger*);

*Blastomyces* (e.g. *Blastomyces dermatitidis*);

*Candida* (e.g. *Candida albicans, Candida glabrata, Candida guilliermondii, Candida krusei, Candida parapsilosis, Candida tropicalis* and *Candida pelliculosa*);

*Cladophialophora* (e.g. *Cladophialophora carrionii*);

*Coccidioides* (e.g. *Coccidioides immitis* and *Coccidioides posadasii*);

*Cryptococcus* (e.g. *Cryptococcus neoformans*);

*Cunninghamella* (e.g. *Cunninghamella* sp.)

*Epidermophyton* (e.g. *Epidermophyton floccosum*);

*Exophiala* (e.g. *Exophiala dermatitidis*);

*Filobasidiella* (e.g. *Filobasidiella neoformans*);

*Fonsecaea* (e.g. *Fonsecaea pedrosoi*);

*Fusarium* (e.g. *Fusarium solani*);

*Geotrichum* (e.g. *Geotrichum candidum*);

*Histoplasma* (e.g. *Histoplasma capsulatum*);

*Hortaea* (e.g. *Hortaea werneckii*);

*Issatschenkia* (e.g. *Issatschenkia orientalis*);

*Madurella* (e.g. *Madurella grisae*);

*Malassezia* (e.g. *Malassezia furfur, Malassezia globosa, Malassezia obtusa, Malassezia pachydermatis, Malassezia restricta, Malassezia slooffiae* and *Malassezia sympodialis*);

*Microsporum* (e.g. *Microsporum canis, Microsporum fulvum* and *Microsporum gypseum*);

*Microsporidia;*

*Mucor* (e.g. *Mucor circinelloides*);

*Nectria* (e.g. *Nectria haematococca*);

*Paecilomyces* (e.g. *Paecilomyces variotii*);

*Paracoccidioides* (e.g. *Paracoccidioides brasiliensis*);

*Penicillium* (e.g. *Penicillium marneffei*);

*Pichia* (e.g. *Pichia anomala* and *Pichia guilliermondii*);

*Pneumocystis* (e.g. *Pneumocystis jiroveci* (*Pneumocystis carinii*));

*Pseudallescheria* (e.g. *Pseudallescheria boydii*);

*Rhizopus* (e.g. *Rhizopus oryzae*);

*Rhodotorula* (e.g. *Rhodotorula rubra*);

*Scedosporium* (e.g. *Scedosporium apiospermum*);

*Schizophyllum* (e.g. *Schizophyllum commune*);

*Sporothrix* (e.g. *Sporothrix schenckii*);

*Trichophyton* (e.g. *Trichophyton mentagrophytes, Trichophyton rubrum, Trichophyton verrucosum* and *Trichophyton violaceum*); and

*Trichosporon* (e.g. *Trichosporon asahii, Trichosporon cutaneum, Trichosporon inkin* and *Trichosporon mucoides*).

Particular bacteria that may treated using a combination of the invention include:

Staphylococci, such as *Staph. aureus* (either Methicillin-sensitive (i.e. MSSA) or Methicillin-resistant (i.e. MRSA)) and *Staph. epidermidis*;

Streptococci, such as *Strept. agalactiae* and *Strept. pyogenes*;

Bacillaceae, such as *Bacillus anthracis*;

Enterobacteriaceae, such as *Escherichia coli*, *Klebsiella* (e.g. *Klebs. pneumoniae* and *Klebs. oxytoca*) and *Proteus* (e.g. *Pr. mirabilis, Pr. rettgeri* and *Pr. vulgaris*);

*Haemophilis influenzae*;

Enterococci, such as *Enterococcus faecalis* and *Enterococcus faecium*; and

*Mycobacteria*, such as *Mycobacterium tuberculosis*.

Preferably, the bacterium is *Staph. Aureus*; either MSSA or MRSA.

Particular fungi that may be treated with a combination of the invention include *Aspergillus fumigatus, Candida albicans, Cryptococcus neoformans, Histoplasma capsulatum* and *Pneumocystis jiroveci*.

The combinations of the present invention may be used to treat infections associated with any of the above-mentioned bacterial or fungal organisms, and in particular they may be used for killing multiplying and/or clinically latent microorganisms associated with such an infection. In one aspect the invention provides the use of an antimicrobial agent in combination with an anesthetic agent for killing clinically latent microorganisms associated with a microbial infection.

Particular conditions which may be treated using the combination of the present invention include tuberculosis (e.g. pulmonary tuberculosis, non-pulmonary tuberculosis (such as tuberculosis lymph glands, genito-urinary tuberculosis, tuberculosis of bone and joints, tuberculosis meningitis) and miliary tuberculosis), anthrax, abscesses, acne vulgaris, actinomycosis, asthma, bacilliary dysentry, bacterial conjunctivitis, bacterial keratitis, bacterial vaginosis, botulism, Buruli ulcer, bone and joint infections, bronchitis (acute or chronic), brucellosis, burn wounds, cat scratch fever, cellulitis, chancroid, cholangitis, cholecystitis, cutaneous diphtheria, cystic fibrosis, cystitis, diffuse panbronchiolitis, diphtheria, dental caries, diseases of the upper respiratory tract, eczema, empymea, endocarditis, endometritis, enteric fever, enteritis, epididymitis, epiglottitis, erysipelis, erysipclas, erysipeloid, erythrasma, eye infections, furuncles, gardnerella vaginitis, gastrointestinal infections (gastroenteritis), genital infections, gingivitis, gonorrhoea, granuloma inguinale, Haverhill fever, infected burns, infections following dental operations, infections in the oral region, infections associated with prostheses, intraabdominal abscesses, Legionnaire's disease, leprosy, leptospirosis, listeriosis, liver abscesses, Lyme disease, lymphogranuloma venerium, mastitis, mastoiditis, meningitis and infections of the nervous system, mycetoma, nocardiosis (e.g. Madura foot), non-specific urethritis, opthalmia (e.g. opthalmia neonatorum), osteomyelitis, otitis (e.g. otitis externa and otitis media), orchitis, pancreatitis, paronychia, pelveoperitonitis, peritonitis, peritonitis with appendicitis, pharyngitis, phlegmons, pinta, plague, pleural effusion, pneumonia, postoperative wound infections, postoperative gas gangrene, prostatitis, pseudo-membranous colitis, psittacosis, pulmonary emphysema, pyelonephritis, pyoderma (e.g. impetigo), Q fever, rat-bite fever, reticulosis, ricin poisoning, Ritter's disease, salmonellosis, salpingitis, septic arthritis, septic infections, septicameia, sinusitis, skin infections (e.g. skin granulomas, impetigo, folliculitis and furunculosis), syphilis, systemic infections, tonsillitis, toxic shock syndrome, trachoma, tularaemia, typhoid, typhus (e.g. epidemic typhus, murine typhus, scrub typhus and spotted fever), urethritis, wound infections, yaws, aspergillosis, candidiasis (e.g. oropharyngeal candidiasis, vaginal candidiasis or balanitis), cryptococcosis, favus, histoplasmosis, intertrigo, mucormycosis, tinea (e.g. tinea corporis, tinea capitis, tinea cruris, tinea pedis and tinea unguium), onychomycosis, pityriasis versicolor, ringworm and sporotrichosis; or infections with MSSA, MRSA, *Staph. epidermidis, Strept. agalactiae, Strept. pyogenes, Escherichia coli, Klebs. pneumoniae, Klebs. oxytoca, Pr. mirabilis, Pr. rettgeri, Pr. vulgaris, Haemophilus influenzae, Enterococcus faecalis* and *Enterococcus faecium*.

In a preferred embodiment of the invention there is provided the use of an anesthetic agent, preferably dyclonine hydrochloride, in combination with an antimicrobial agent, preferably 4-methyl-1-(2-phenylethyl)-8-phenoxy-2,3-dihydro-1H-pyrrolo[3,2-c]-quinoline or a pharmaceutically acceptable derivative thereof, for nasal decolonisation of MSSA or MRSA, preferably MRSA, in particular for killing clinically latent microorganisms associated with such an infection.

It will be appreciated that references herein to "treatment" extend to prophylaxis as well as the treatment of established diseases or symptoms.

Suitable antimicrobial compounds for use in the present invention include one or more compounds selected from the following:

(1) β-Lactams, including:
  (i) penicillins, such as
   (I) benzylpenicillin, procaine benzylpenicillin, phenoxy-methylpenicillin, methicillin, propicillin, epicillin, cyclacillin, hetacillin, 6-aminopenicillanic acid, penicillic acid, penicillanic acid sulphone (sulbactam), penicillin G, penicillin V, phenethicillin, phenoxymethylpenicillinic acid, azlocillin, carbenicillin, cloxacillin, D-(-)-penicillamine, dicloxacillin, nafcillin and oxacillin,
   (II) penicillinase-resistant penicillins (e.g. flucloxacillin),
   (III) broad-spectrum penicillins (e.g. ampicillin, amoxicillin, metampicillin and bacampicillin),
   (IV) antipseudomonal penicillins (e.g. carboxypenicillins such as ticarcillin or ureidopenicillins such as piperacillin),
   (V) mecillinams (e.g. pivmecillinam), or
   (VI) combinations of any two or more of the agents mentioned at (I) to (V) above, or combinations of any of the agents mentioned at (I) to (V) above with a β-lactamase inhibitor such as tazobactam or, particularly, clavulanic acid (which acid is optionally in metal salt form, e.g. in salt form with an alkali metal such as sodium or, particularly, potassium);
  (ii) cephalosporins, such as cefaclor, cefadroxil, cefalexin (cephalexin), cefcapene, cefcapene pivoxil, cefdinir, cefditoren, cefditoren pivoxil, cefixime, cefotaxime, cefpirome, cefpodoxime, cefpodoxime proxetil, cefprozil, cefradine, ceftazidime, cefteram, cefteram pivoxil, ceftriaxone, cefuroxime, cefuroxime axetil, cephaloridine, cephacetrile, cephamandole, cephaloglycine, ceftobiprole, PPI-0903 (TAK-599), 7-aminocephalosporanic acid, 7-aminodes-acetoxycephalosporanic acid, cefamandole, cefazolin, cefmetazole, cefoperazone, cefsulodin, cephalosporin C zinc salt, cephalothin, cephapirin; and
  (iii) other β-lactams, such as monobactams (e.g. aztreonam), carbapenems (e.g. imipenem (optionally in combination with a renal enzyme inhibitor such as cilastatin), meropenem, ertapenem, doripenem (S-4661) and RO4908463. (CS-023)), penems (e.g. faropenem) and 1-oxa-β-lactams (e.g. moxalactam).
(2) Tetracyclines, such as tetracycline, demeclocycline, doxycycline, lymecycline, minocycline, oxytetracycline, chlortetracycline, meclocycline and methacycline, as well as glycylcyclines (e.g. tigecycline).
(3) Aminoglycosides, such as amikacin, gentamicin, netilmicin, neomycin, streptomycin, tobramycin, amastatin, butirosin, butirosin A, daunorubicin, dibekacin, dihydrostreptomycin, G 418, hygromycin B, kanamycin B, kanamycin, kirromycin, paromomycin, ribostamycin, sisomicin, spectinomycin, streptozocin and thiostrepton.
(4) (i) Macrolides, such as azithromycin, clarithromycin, erythromycin, roxithromycin, spiramycin, amphotericins B (e.g. amphotericin B), bafilomycins (e.g. bafilomycin A1), brefeldins (e.g. brefeldin A), concanamycins (e.g. concanamycin A), filipin complex, josamycin, mepartricin, midecamycin, nonactin, nystatin, oleandomycin, oligomycins (e.g. oligomycin A, oligomycin B and oligomycin C), pimaricin, rifampicin, rifamycin, rosamicin, tylosin, virginiamycin and fosfomycin.
  (ii) Ketolides such as telithromycin and cethromycin (ABT-773).
  (iii) Lincosamines, such as lincomycin.
(5) Clindamycin and clindamycin 2-phosphate.
(6) Phenicols, such as chloramphenicol and thiamphenicol.
(7) Steroids, such as fusidic acid (optionally in metal salt form, e.g. in salt form with an alkali metal such as sodium).
(8) Glycopeptides such as vancomycin, teicoplanin, bleomycin, phleomycin, ristomycin, telavancin, dalbavancin and oritavancin.
(9) Oxazolidinones, such as linezolid and AZD2563.
(10) Streptogramins, such as quinupristin and dalfopristin, or a combination thereof.
(11) (i) Peptides, such as polymyxins (e.g. colistin and polymyxin B), lysostaphin, duramycin, actinomycins (e.g. actinomycin C and actinomycin D), actinonin, 7-aminoactinomycin D, antimycin A, antipain, bacitracin, cyclosporin A, echinomycin, gramicidins (e.g. gramicidin A and gramicidin C), myxothiazol, nisin, paracelsin, valinomycin and viomycin.
  (ii) Lipopeptides, such as daptomycin.
  (iii) Lipoglycopeptides, such as ramoplanin.
(12) Sulfonamides, such as sulfamethoxazole, sulfadiazine, sulfaquinoxaline, sulfathiazole (which latter two agents are optionally in metal salt form, e.g. in salt form with an alkali metal such as sodium), succinylsulfathiazole, sulfadimethoxine, sulfaguanidine, sulfamethazine, sulfamonomethoxine, sulfanilamide and sulfasalazine.
(13) Trimethoprim, optionally in combination with a sulfonamide, such as sulfamethoxazole (e.g. the combination co-trimoxazole).
(14) Antituberculous drugs, such as isoniazid, rifampicin, rifabutin, pyrazinamide, ethambutol, streptomycin, amikacin, capreomycin, kanamycin, quinolones (e.g. those at (q) below), para-aminosalicylic acid, cycloserine and ethionamide.
(15) Antileprotic drugs, such as dapsone, rifampicin and clofazimine.
(16) (i) Nitroimidazoles, such as metronidazole and timidazole.
  (ii) Nitrofurans, such as nitrofurantoin.
(17) Quinolones, such as nalidixic acid, norfloxacin, ciprofloxacin, ofloxacin, levofloxacin, moxifloxacin, gatifloxacin, gemifloxacin, garenoxacin, DX-619, WCK 771 (the arginine salt of S-(−)-nadifloxacin), 8-quinolinol, cinoxacin, enrofloxacin, flumequine, lomefloxacin, oxolinic acid and pipemidic acid.
(18) Amino acid derivatives, such as azaserine, bestatin, D-cycloserine, 1,10-phenanthroline, 6-diazo-5-oxo-L-norleucine and L-alanyl-L-1-aminoethyl-phosphonic acid.
(19) Aureolic acids, such as chromomycin A3, mithramycin A and mitomycin C.
(20) Benzochinoides, such as herbimycin A.
(21) Coumarin-glycosides, such as novobiocin.
(22) Diphenyl ether derivatives, such as irgasan.
(23) Epipolythiodixopiperazines, such as gliotoxin from *Gliocladium fimbriatum*.
(24) Fatty acid derivatives, such as cerulenin.
(25) Glucosamines, such as 1-deoxymannojirimycin, 1-deoxynojirimycin and N-methyl-1-deoxynojirimycin.
(26) Indole derivatives, such as staurosporine.
(27) Diaminopyrimidines, such as iclaprim (AR-100).
(28) Macrolactams, such as ascomycin.
(29) Taxoids, such as paclitaxel.
(30) Statins, such as mevastatin.
(31) Polyphenolic acids, such as (+)-usnic acid.
(32) Polyethers, such as lasalocid A, lonomycin A, monensin, nigericin and salinomycin.
(33) Picolinic acid derivatives, such as fusaric acid.
(34) Peptidyl nucleosides, such as blasticidine S, nikkomycin, nourseothricin and puromycin.
(35) Nucleosides, such as adenine 9-β-D-arabinofuranoside, 5-azacytidine, cordycepin, formycin A, tubercidin and tunicamycin.
(36) Pleuromutilins, such as GSK-565154, GSK-275833 and tiamulin.
(37) Peptide deformylase inhibitors, such as LBM415 (NVP PDF-713) and BB 83698.
(38) Antibacterial agents for the skin, such as fucidin, benzamycin, clindamycin, erythromycin, tetracycline, silver sulfadiazine, chlortetracycline, metronidazole, mupirocin, framycitin, gramicidin, neomycin sulfate, polymyxins (e.g. polymixin B) and gentamycin.
(39) Miscellaneous agents, such as methenamine (hexamine), doxorubicin, piericidin A, stigmatellin, actidione, anisomycin, apramycin, coumermycin A1, L(+)-lactic acid, cytochalasins (e.g. cytochalasin B and cytochalasin D), emetine and ionomycin.
(40) Antiseptic agents, such as chlorhexidine, phenol derivatives (e.g. thymol and triclosan), quarternary ammonium compounds (e.g. benzalkonium chloride, cetylpyridinium chloride, benzethonium chloride, cetrimonium bromide, cetrimonium chloride and cetrimonium stearate), octenidine dihydrochloride, and terpenes (e.g. terpinen-4-ol).

In one embodiment of the present invention, the antimicrobial agent is selected from any one of the above-mentioned groups (1) to (40). In another embodiment, the antimicrobial agent is selected from any one of the above-mentioned groups (1) to (39), i.e. the antimicrobial agent is not an antiseptic agent. A particularly preferred antimicrobial compound is mupirocin or a pharmaceutically acceptable derivative thereof.

Further preferred antimicrobial compounds for use in the present invention are those capable of killing clinically latent microorganisms. Methods for determining activity against clinically latent bacteria include a determination, under conditions known to those skilled in the art (such as those described in *Nature Reviews, Drug Discovery*, 1, 895-910 (2002), the disclosures of which are hereby incorporated by reference), of Minimum Stationary-cidal Concentration ("MSC") or Minimum Dormicidal Concentration ("MDC") for a test compound. A suitable compound screening method against clinically latent microorganisms is described in WO2000028074, the contents of which are incorporated herein by reference as if the publication was specifically and fully set forth herein.

Examples of compounds capable of killing clinically latent microorganisms include those compounds disclosed in International Patent Application, Publication Numbers WO2007054693, WO2008117079 and WO2008142384. These applications describe suitable methods for the preparation of such compounds and doses for their administration.

Preferred examples of antimicrobial agents for use in the present invention include a compound selected from the group consisting of:

6,8-dimethoxy-4-methyl-1-(3-phenoxyphenyl)-2,3-dihydro-1H-pyrrolo[3,2-c]-quinoline;
6,8-dimethoxy-4-methyl-1-(2-phenoxyethyl)-2,3-dihydro-1H-pyrrolo[3,2-c]-quinoline;
1-cyclopropyl-6,8-dimethoxy-4-methyl-2,3-dihydro-1H-pyrrolo[3,2-c]-quinoline;
8-methoxy-4-methyl-1-(4-phenoxyphenyl)-2,3-dihydro-1H-pyrrolo[3,2-c]-quinoline;
{2-[4-(8-methoxy-4-methyl-2,3-dihydro-1H-pyrrolo[3,2-d]quinolin-1-yl)-phenyoxy]ethyl}dimethylamine;
8-methoxy-4-methyl-1-[4-(pyridin-3-yloxy)phenyl]-2,3-dihydro-1H-pyrrolo[3,2-c]quinoline;
4-methyl-8-phenoxy-1-phenyl-2,3-dihydro-1H-pyrrolo[3,2-c]quinoline;
1-benzyl-4-methyl-8-phenoxy-2,3-dihydro-1H-pyrrolo[3,2-c]quinoline
1-(indan-2-yl)-4-methyl-8-phenoxy-2,3-dihydro-1H-pyrrolo[3,2-c]quinoline
4-methyl-6-phenoxy-1-phenyl-2,3-dihydro-1H-pyrrolo[3,2-c]quinoline;
1-benzyl-4-methyl-6-phenoxy-2,3-dihydro-1H-pyrrolo[3,2-c]quinoline;
1-(indan-2-yl)-4-methyl-6-phenoxy-2,3-dihydro-1H-pyrrolo[3,2-c]quinoline;
4-methyl-1-(2-phenylethyl)-8-phenoxy-2,3-dihydro-1H-pyrrolo[3,2-c]-quinoline;
8-methoxy-4-methyl-1-(2-phenylethyl)-2,3-dihydro-1H-pyrrolo[3,2-c]-quinolin-6-ol;
1-(1-benzyl-piperidin-4-yl)-4-methyl-8-phenoxy-2,3-dihydro-1H-pyrrolo[3,2-c]quinoline;
1-(indan-1-yl)-4-methyl-8-phenoxy-2,3-dihydro-1H-pyrrolo[3,2-c]quinoline;
1-(benzodioxan-2-ylmethyl)-4-methyl-8-phenoxy-2,3-dihydro-1H-pyrrolo[3,2-c]quinoline;
4-methyl-8-phenoxy-1-(1,2,3,4-tetrahydronaphthalen-1-yl)-2,3-dihydro-1H-pyrrolo[3,2-c]quinoline;
1-cyclohexyl-4-methyl-8-phenoxy-2,3-dihydro-1H-pyrrolo[3,2-c]quinoline;
8-ethoxy-4-methyl-1-(4-phenoxyphenyl)-2,3-dihydro-1H-pyrrolo[3,2-c]-quinoline;
1-(4-methoxyphenyl)-4-methyl-8-phenoxy-2,3-dihydro-1H-pyrrolo[3,2-c]-quinoline;
4-methyl-1-(4-phenoxyphenyl)-2,3-dihydro-1H-pyrrolo[3,2-c]quinoline;
4-methyl-1-(2-methylphenyl)methyl-8-phenoxy-2,3-dihydro-1H-pyrrolo[3,2-c]quinoline;
4-methyl-8-phenoxy-1-(4-iso-propylphenyl)-1H-pyrrolo[3,2-c]-quinoline;
4-methyl-8-phenoxy-1-(1-phenylethyl)-2,3-dihydro-1H-pyrrolo[3,2-c]-quinoline;
8-methoxy-4-methyl-1-(2-phenylethyl)-2,3-dihydro-1H-pyrrolo[3,2-c]-quinoline;
6,8-dimethoxy-1-(4-hydroxyphenyl)-4-methyl-2,3-dihydro-1H-pyrrolo[3,2-c]quinoline;
6,8-dimethoxy-1-(3-hydroxyphenyl)-4-methyl-2,3-dihydro-1H-pyrrolo[3,2-c]quinoline;
6,8-dimethoxy-1-(3-hydroxy-5-methylphenyl)-4-methyl-2,3-dihydro-1H-pyrrolo[3,2-c]quinoline;
8-methoxy-1-(4-methoxyphenyl)-4-methyl-2,3-dihydro-1H-pyrrolo[3,2-c]-quinoline;
8-trifluoromethoxy-1-(4-phenoxyphenyl)-4-methyl-2,3-dihydro-1H-pyrrolo[3,2-c]quinoline;
6,8-dimethoxy-4-methyl-1-[4-(pyridin-3-yloxy)phenyl]-2,3-dihydro-1H-pyrrolo[3,2-c]quinoline;
1-benzyl-6,8-dimethoxy-4-methyl-2,3-dihydro-1H-pyrrolo[3,2-c]quinoline;
6,8-dimethoxy-4-methyl-1-(2-phenylethyl)-1H-pyrrolo[3,2-c]quinoline;
4-methyl-1-(2-phenylethyl)-8-trifluoromethoxy-2,3-dihydro-1H-pyrrolo[3,2-c]quinoline;
6,8-dimethoxy-1-(indan-1-yl)-4-methyl-2,3-dihydro-1H-pyrrolo[3,2-c]-quinoline;
6,8-dimethoxy-4-methyl-1-[(6-phenoxy)pyridin-3-yl]-2,3-dihydro-1H-pyrrolo[3,2-c]quinoline;
6,8-dimethoxy-1-[(6-methoxy)pyridin-3-yl]-4-methyl-2,3-dihydro-1H-pyrrolo[3,2-c]quinoline;
1-(benzodioxol-5-ylmethyl)-6,8-dimethoxy-4-methyl-2,3-dihydro-1H-pyrrolo[3,2-c]quinoline;
6,8-dimethoxy-4-methyl-1-(3-methylbutyl)-2,3-dihydro-1H-pyrrolo[3,2-c]quinoline;
1-cyclopropylmethyl-6,8-dimethoxy-4-methyl-2,3-dihydro-1H-pyrrolo[3,2-c]quinoline;
4-methyl-8-(morpholin-4-yl)-1-(4-phenoxyphenyl)-2,3-dihydro-1H-pyrrolo[3,2-c]quinoline;
8-methoxy-4-methyl-1-(1,2,3,4-tetrahydronaphthalen-1-yl)-2,3-dihydro-1H-pyrrolo[3,2-c]quinoline;
4-methyl-1-(2-phenylethyl)-2,3-dihydro-1H-pyrrolo[3,2-c]quinoline;
4,6-dimethyl-1-(2-methylphenyl)-2,3-dihydro-1H-pyrrolo[3,2-c]quinoline;
4,6-dimethyl-1-(2-phenylethyl)-2,3-dihydro-1H-pyrrolo[3,2-c]quinoline;
4-methyl-8-(piperidin-1-yl)-1-[4-(piperidin-1-yl)phenyl]-2,3-dihydro-1H-pyrrolo[3,2-c]quinoline;
4-methyl-8-(piperidin-1-yl)-1-(3-phenoxyphenyl)-2,3-dihydro-1H-pyrrolo[3,2-c]quinoline;
1-{4-[2-(N,N-dimethylamino)ethoxy]phenyl}-4-methyl-8-phenoxy-2,3-dihydro-1H-pyrrolo[3,2-c]quinoline;
1-[4-(4-fluorophenoxy)phenyl]-8-methoxy-4-methyl-2,3-dihydro-1H-pyrrolo[3,2-c]quinoline;
1-(benzodioxan-2-ylmethyl)-8-methoxy-4-methyl-2,3-dihydro-1H-pyrrolo[3,2-c]quinoline;
1-cyclohexyl-8-methoxy-4-methyl-2,3-dihydro-1H-pyrrolo[3,2-c]quinoline;
8-methoxy-4-methyl-1-phenyl-2,3-dihydro-1H-pyrrolo[3,2-c]quinoline;
4-methyl-8-phenoxy-1-[4-(3-pyridyl)phenyl]-2,3-dihydro-1H-pyrrolo[3,2-c]quinoline;
4-methyl-8-phenoxy-1-[2-(3-pyridyl)ethyl]-2,3-dihydro-1H-pyrrolo[3,2-c]quinoline;
4-methyl-8-phenoxy-1-(2-pyridylmethyl)-2,3-dihydro-1H-pyrrolo[3,2-c]-quinoline;
4-methyl-1-(5-methylpyrazin-2-ylmethyl)-8-phenoxy-2,3-dihydro-1H-pyrrolo[3,2-c]quinoline;
8-chloro-4-methyl-1-(2-phenylethyl)-2,3-dihydro-1H-pyrrolo[3,2-c]-quinoline;
4-methyl-1-(2-phenylethyl)-2,3-dihydro-1H-pyrrolo[3,2-c]quinoline-8-carboxylate;

4-methyl-8-(morpholin-1-yl)-1-(2-phenylethyl)-2,3-dihydro-1H-pyrrolo[3,2-c]quinoline;
ethyl [4-methyl-1-(2-phenylethyl)-2,3-dihydro-1H-pyrrolo[3,2-c]quinoline-8-yl]acetate;
1-[3-(4-methyl-8-phenoxy-2,3-dihydro-1H-pyrrolo[3,2-c]quinolin-1-yl)propyl]-pyrrolidin-2-one;
4-methyl-8-phenoxy-1-[2-(2-pyridyl)ethyl]-2,3-dihydro-1H-pyrrolo[3,2-c]quinoline;
ethyl 3-(8-methoxy-4-methyl-2,3-dihydro-1H-pyrrolo[3,2-c]quinoline-1-yl)propionate;
ethyl 4-(4-methyl-8-phenoxy-2,3-dihydro-1H-pyrrolo[3,2-c]quinoline-1-yl)butanoate;
methyl 4-(4-methyl-8-phenoxy-2,3-dihydro-1H-pyrrolo[3,2-c]quinoline-1-yl)butanoate;
ethyl (4-methyl-8-phenoxy-2,3-dihydro-1H-pyrrolo[3,2-c]quinoline-1-yl)acetate;
4-methyl-1-(1-methylpiperidin-4-yl)-8-phenoxy-2,3-dihydro-1H-pyrrolo[3,2-c]quinoline;
1-(1-benzylpyrrolidin-3-yl)-8-methoxy-4-methyl-2,3-dihydro-1H-pyrrolo[3,2-c]quinoline;
methyl 3-(4-methyl-8-phenoxy-2,3-dihydro-1H-pyrrolo[3,2-c]quinoline-1-yl)propionate;
1-((S)-indan-1-yl)-4-methyl-8-phenoxy-2,3-dihydro-1H-pyrrolo[3,2-c]-quinoline;
1-((R)-indan-1-yl)-4-methyl-8-phenoxy-2,3-dihydro-1H-pyrrolo[3,2-c]-quinoline;
1-(3-methoxypropyl)-4-methyl-8-phenoxy-2,3-dihydro-1H-pyrrolo[3,2-c]-quinoline;
4-methyl-8-phenoxy-1-(tetrahydrofuran-2-ylmethyl)-2,3-dihydro-1H-pyrrolo[3,2-c]quinoline;
1-[2-(4-chlorophenyl)ethyl]-4-methyl-8-phenoxy-2,3-dihydro-1H-pyrrolo[3,2-c]quinoline;
1-[2-(4-methoxyphenyl)ethyl]-4-methyl-8-phenoxy-2,3-dihydro-1H-pyrrolo[3,2-c]quinoline;
4-methyl-8-phenoxy-1-(2-phenylpropyl)-2,3-dihydro-1H-pyrrolo[3,2-c]-quinoline;
8-cyano-4-methyl-1-(2-phenylethyl)-2,3-dihydro-1H-pyrrolo[3,2-c]quinoline;
8-hydroxy-4-methyl-1-(2-phenylethyl)-2,3-dihydro-1H-pyrrolo[3,2-c]-quinoline;
8-phenoxy-1-(2-phenylethyl)-2,3-dihydro-1H-pyrrolo[3,2-c]quinoline;
6,8-dimethoxy-1-(4-hydroxyphenyl)-4-methylpyrrolo[3,2-c]quinoline;
8-methoxy-4-methyl-1-[4-(4-methylpiperazin-1-yl)-3-fluorophenyl]-2,3-dihydro-1H-pyrrolo[3,2-c]quinoline;
4-methyl-8-phenylamino-1-(2-phenylethyl)-2,3-dihydro-1H-pyrrolo[3,2-c]-quinoline;
[4-methyl-1-(2-phenylethyl)-2,3-dihydro-1H-pyrrolo[2,3-c]quinoline-8-oyl]-piperidine;
6,8-dimethoxy-1-(4-iso-propylphenyl)-4-methyl-2,3-dihydro-1H-pyrrolo[3,2-c]quinoline;
6-methoxy-1-(4-phenoxyphenyl)-4-methyl-2,3-dihydro-1H-pyrrolo[3,2-c]quinoline;
6-methoxy-1-(4-iso-propylphenyl)-4-methyl-2,3-dihydro-1H-pyrrolo[3,2-c]quinoline;
6,8-dimethoxy-1-(4-phenoxyphenyl)-4-methyl-2,3-dihydro-1H-pyrrolo[3,2-c]quinoline;
4-methyl-8-phenoxy-1-(4-phenoxyphenyl)-2,3-dihydro-1H-pyrrolo[3,2-c]quinoline;
1-(4-iso-propylphenyl)-6-phenoxy-4-methyl-2,3-dihydro-1H-pyrrolo[3,2-c]quinoline; and
4,6-dimethyl-1-(4-methylphenyl)-2,3-dihydro-1H-pyrrolo[3,2-c]quinoline;
or a pharmaceutically acceptable derivative thereof.

Further preferred examples of antimicrobial agents include a compound selected from the group consisting of:
(1-methyl-1H-benzimidazol-2-yl)-(6-hydroxy-2-methylquinolin-4-yl)amine;
(1-methyl-1H-benzimidazol-2-yl)-(2-methyl-6-phenoxyquinolin-4-yl)amine;
(1-methyl-1H-benzimidazol-2-yl)-(6-chloro-2-methylquinolin-4-yl)amine;
(1-methyl-1H-benzimidazol-2-yl)-(6-cyano-2-methylquinolin-4-yl)amine;
(1-methyl-1H-benzimidazol-2-yl)-(6-benzyloxy-2-methylquinolin-4-yl)amine;
(1-methyl-1H-benzimidazol-2-yl)-(5,6-dichloro-2-methylquinolin-4-yl)amine;
(1-methyl-1H-benzimidazol-2-yl)-(7-chloro-2-methylquinolin-4-yl)amine hydrochloride;
(1-methyl-1H-benzimidazol-2-yl)-(6,8-dichloro-2-methylquinolin-4-yl)amine;
[6-(4-fluorophenoxy)-2-methylquinolin-4-yl]-(1-methyl-1H-benzimidazol-2-yl)amine;
(2-methyl-6-phenylaminoquinolin-4-yl)-(1-methyl-1H-benzimidazol-2-yl)amine;
(1H-benzimidazol-2-yl)-(2-methyl-6-phenoxyquinolin-4-yl)-amine;
(benzoxazol-2-yl)-(2-methyl-6-phenoxyquinolin-4-yl)amine;
(1H-benzimidazol-2-yl)-(6-chloro-2-methylquinazolin-4-yl)amine;
[2-methyl-6-(pyrimidin-2-yloxy)quinolin-4-yl]-(1-methyl-1H-benzimidazol-2-yl)amine;
(1-methyl-1H-benzimidazol-2-yl)-[2-methyl-6-(4-methylpiperazin-1-yl)-quinolin-4-yl]amine; and
(1-methyl-1H-benzimidazol-2-yl)-(2-morpholin-4-yl-6-phenoxyquinolin-4-yl)amine;
or a pharmaceutically acceptable derivative thereof.

Still further preferred examples of antimicrobial agents include a compound selected from the group consisting of:
6-chloro-2-methyl-4-(3-phenylpyrrolidin-1-yl)quinoline;
6-benzyloxy-2-methyl-4-(3-phenylpyrrolidin-1-yl)quinoline;
2-methyl-4-(3-phenylpyrrolidin-1-yl)-6-(pyridin-3-ylmethoxy)quinoline;
6-(4-methanesulfonylbenzyloxy)-2-methyl-4-(3-phenylpyrrolidin-1-yl)quinoline;
6-(4-methoxybenzyloxy)-2-methyl-4-(3-phenylpyrrolidin-1-yl)quinoline
2-methyl-6-phenethyloxy-4-(3-phenylpyrrolidin-1-yl)quinoline;
2-methyl-6-(5-methylisoxazol-3-ylmethoxy)-4-(3-phenylpyrrolidin-1-yl)quinoline;
4-(3-benzylpyrrolidin-1-yl)-2-methyl-6-phenoxyquinoline;
4-[3-(4-methoxyphenyl)pyrrolidin-1-yl]-2-methyl-6-phenoxyquinoline;
4-[3-(4-chlorophenyl)pyrrolidin-1-yl]-2-methyl-6-phenoxyquinoline;
[1-(2-methyl-6-phenoxyquinolin-4-yl)-pyrrolidin-3-yl]phenylamine;
N-[2-methyl-4-(3-phenylpyrrolidin-1-yl)quinolin-6-yl]benzamide;
N-[2-methyl-4-(3-phenylpyrrolidin-1-yl)-quinolin-6-yl]-2-phenylacetamide;
4-chloro-N-[2-methyl-4-(3-phenylpyrrolidin-1-yl)quinolin-6-yl]benzamide;
4-methoxy-N-[2-methyl-4-(3-phenylpyrrolidin-1-yl)quinolin-6-yl]benzamide;
2-methyl-N-[2-methyl-4-(3-phenylpyrrolidin-1-yl)quinolin-6-yl]benzamide;
pyrazine-2-carboxylic acid [2-methyl-4-(3-phenylpyrrolidin-1-yl)quinolin-6-yl]amide;

1H-pyrazole-4-carboxylic acid [2-methyl-4-(3-phenylpyrrolidin-1-yl)quinolin-6-yl]amide;
furan-2-carboxylic acid [2-methyl-4-(3-phenylpyrrolidin-1-yl)quinolin-6-yl]amide;
N-[2-methyl-4-(3-phenylpyrrolidin-1-yl)quinolin-6-yl]nicotinamide;
3-methyl-3H-imidazole-4-carboxylic acid [2-methyl-4-(3-phenylpyrrolidin-1-yl)quinolin-6-yl]amide;
5-methyl-1H-pyrazole-3-carboxylic acid [2-methyl-4-(3-phenylpyrrolidin-1-yl)-quinolin-6-yl]amide;
pyridazine-4-carboxylic acid [2-methyl-4-(3-phenylpyrrolidin-1-yl)-quinolin-6-yl]amide;
2-(4-methoxyphenyl)-N-[2-methyl-4-(3-phenylpyrrolidin-1-yl)quinolin-6-yl]acetamide;
2-(4-chlorophenyl)-N-[2-methyl-4-(3-phenylpyrrolidin-1-yl)quinolin-6-yl]acetamide;
3,5-dimethyl-isoxazole-4-carboxylic acid [2-methyl-4-(3-phenylpyrrolidin-1-yl)quinolin-6-yl]amide;
2-(3-methyl-isoxazol-5-yl)-N-[2-methyl-4-(3-phenyl-pyrrolidin-1-yl)-quinolin-6-yl]-acetamide;
N-[2-methyl-4-(3-phenylpyrrolidin-1-yl)quinolin-6-yl]benzenesulfonamide;
benzyl-[2-methyl-4-(3-phenylpyrrolidin-1-yl)quinolin-6-yl]amine;
(R- or S-)Benzyl-[2-methyl-4-(3-phenylpyrrolidin-1-yl)quinolin-6-yl]amine;
(S- or R-)Benzyl-[2-methyl-4-(3-phenylpyrrolidin-1-yl)quinolin-6-yl]amine;
(4-methoxybenzyl)-[2-methyl-4-(3-phenylpyrrolidin-1-yl)quinolin-6-yl]amine;
4-{[2-methyl-4-(3-phenylpyrrolidin-1-yl)quinolin-6-ylamino]methyl}benzonitrile;
1-[2-methyl-4-(3-phenylpyrrolidin-1-yl)quinolin-6-yl]pyrrolidin-2-one;
N-[2-methyl-4-(3-phenylpyrrolidin-1-yl)quinolin-6-yl]-3-phenyl propionamide;
5-methyl-isoxazole-3-carboxylic acid [2-methyl-4-(3-phenylpyrrolidin-1-yl)-quinolin-6-yl]amide;
pyridine-2-carboxylic acid [2-methyl-4-(3-phenylpyrrolidin-1-yl)quinolin-6-yl]amide;
N-[4-(3-benzylpyrrolidin-1-yl)-2-methylquinolin-6-yl]benzamide; and
2-methyl-6-phenoxy-4-(3-phenylpyrrolidin-1-yl)quinoline;
or
or a pharmaceutically acceptable derivative thereof.

Particularly preferred antimicrobial agents for use in the present invention are 4-methyl-1-(2-phenylethyl)-8-phenoxy-2,3-dihydro-1H-pyrrolo[3,2-c]-quinoline (Example 9, WO2007054693), 4-(3-benzylpyrrolidin-1-yl)-2-methyl-6-phenoxyquinoline (Example 8, WO2008142384), and N-[4-(3-benzylpyrrolidin-1-yl)-2-methylquinolin-6-yl]benzamide (Example 38, WO2008142384), and pharmaceutically acceptable derivatives thereof. In one embodiment of the invention the antimicrobial agent is 4-(3-benzylpyrrolidin-1-yl)-2-methyl-6-phenoxyquinoline, N-[4-(3-benzyl pyrrolidin-1-yl)-2-methylquinolin-6-yl]benzamide or a pharmaceutically acceptable derivative thereof. A more preferred antimicrobial agent is 4-methyl-1-(2-phenylethyl)-8-phenoxy-2,3-dihydro-1H-pyrrolo[3,2-c]-quinoline or a pharmaceutically acceptable derivative thereof.

References herein to 4-methyl-1-(2-phenylethyl)-8-phenoxy-2,3-dihydro-1H-pyrrolo[3,2-c]-quinoline mean a compound having the following chemical structure:

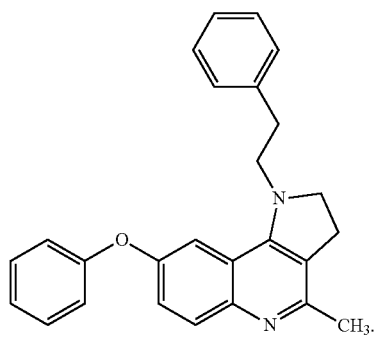 [SMILES: Cc1nc2ccc(Oc3ccccc3)cc2c2c1CCN2CCc1ccccc1]

References herein to 4-(3-benzylpyrrolidin-1-yl)-2-methyl-6-phenoxyquinoline mean a compound having the following chemical structure:

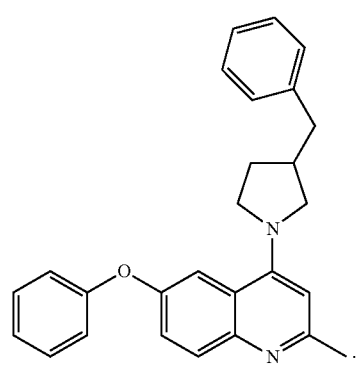 [SMILES: Cc1cc(N2CCC(Cc3ccccc3)C2)c2cc(Oc3ccccc3)ccc2n1]

References herein to N-[4-(3-benzylpyrrolidin-1-yl)-2-methylquinolin-6-yl]benzamide mean a compound having the following chemical structure:

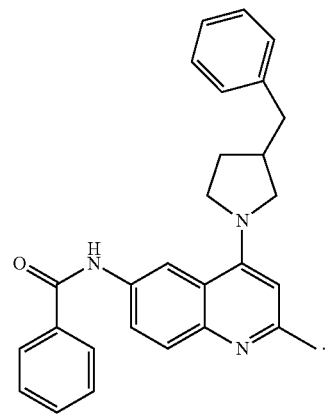 [SMILES: Cc1cc(N2CCC(Cc3ccccc3)C2)c2cc(NC(=O)c3ccccc3)ccc2n1]

Preferred antimicrobial agents of the present invention may be prepared according to the methods disclosed in International Patent Application, Publication Numbers WO2007054693, WO2008117079 and WO2008142384. The contents of these documents are incorporated herein by reference as if each individual publication was specifically and fully set forth herein.

As used herein the term "pharmaceutically acceptable derivative" means:
(a) pharmaceutically acceptable salts with either acids or bases (e.g. acid addition salts); and/or (b) solvates (including hydrates).

Acid addition salts that may be mentioned include carboxylate salts (e.g. formate, acetate, trifluoroacetate, propionate, isobutyrate, heptanoate, decanoate, caprate, caprylate, stearate, acrylate, caproate, propiolate, ascorbate, citrate, glucuronate, glutamate, glycolate, α-hydroxybutyrate, lactate, tartrate, phenylacetate, mandelate, phenylpropionate, phenylbutyrate, benzoate, chlorobenzoate, methyl benzoate, hydroxybenzoate, methoxybenzoate, dinitrobenzoate, o-acetoxybenzoate, salicylate, nicotinate, isonicotinate, cinnamate, oxalate, malonate, succinate, suberate, sebacate, fumarate, malate, maleate, hydroxymaleate, hippurate, phthalate or terephthalate salts), halide salts (e.g. chloride, bromide or iodide salts), sulfonate salts (e.g. benzenesulfonate, methyl-, bromo- or chloro-benzenesulfonate, xylenesulfonate, methanesulfonate, ethanesulfonate, propanesulfonate, hydroxyethanesulfonate, 1- or 2-naphthalenesulfonate or 1,5-naphthalenedisulfonate salts) or sulfate, pyrosulfate, bisulfate, sulfite, bisulfite, phosphate, monohydrogenphosphate, dihydrogenphosphate, metaphosphate, pyrophosphate or nitrate salts, and the like.

A preferred acid addition salt of 4-methyl-1-(2-phenylethyl)-8-phenoxy-2,3-dihydro-1H-pyrrolo[3,2-c]-quinoline is the hydrochloride salt thereof.

Suitable anesthetic agents for use in the present invention include those capable of killing multiplying and/or clinically latent microorganisms. The anesthetic agent may be a general anesthetic agent or a local anesthetic agent or a combination of such agents.

Examples of suitable general anesthetic agents include acepromazine, benzodiazepines such as diazepam and midazolam; etomidate, ketamine, medetomidine, methohexital (methohexitone), propofol, thiopental sodium (thiopentone sodium), tiletamine, xylazine, and combinations thereof.

Thus, in a preferred embodiment the present invention provides the use of acepromazine, a benzodiazepine, etomidate, ketamine, medetomidine, methohexital (methohexitone), propofol, thiopental sodium (thiopentone sodium), tiletamine, xylazine, or a combination thereof for use in killing clinically latent microorganisms associated with a microbial infection.

Examples of suitable local anesthetic agents include aminoamide- and aminoester-derived local anesthetics and combinations thereof. Aminoester derivatives include benzocaine, chloroprocaine, cocaine, cyclomethycaine, dimethocaine (larocaine), propoxycaine, procaine (novocaine), proparacaine, tetracaine (amethocaine) and combinations thereof. Aminoamide derivatives include articaine, bupivacaine, cinchocaine (dibucaine), etidocaine, levobupivacaine, lidocaine (lignocaine), mepivacaine, piperocaine, prilocalne, ripovacaine, trimecaine and combinations thereof. An example of a suitable combination of local anesthetics is lidocaine and prilocalne.

Thus, in a preferred embodiment the present invention provides the use of benzocaine, chloroprocaine, cocaine, cyclomethycaine, dimethocaine (larocaine), propoxycaine, procaine (novocaine), proparacaine, tetracaine (amethocaine), articaine, bupivacaine, cinchocaine (dibucaine), etidocaine, levobupivacaine, lidocaine (lignocaine), mepivacaine, piperocaine, prilocalne, ripovacaine, trimecaine or a combination thereof for use in killing clinically latent microorganisms associated with a microbial infection.

A particularly preferred local anesthetic is dyclonine (1-(4-Butoxyphenyl)-3-(1-piperidinyl)-1-propanone) hydrochloride. Dyclonine hydrochloride is commercially available from Sigma-Aldrich Co. (Fluka). Thus, the present invention also provides the use of dyclonine or a pharmaceutically acceptable derivative thereof, particularly dyclonine hydrochloride, for use in killing clinically latent microorganisms associated with a microbial infection.

According to a preferred embodiment of the invention there is provided a combination comprising an antimicrobial agent selected from the group consisting of 4-methyl-1-(2-phenylethyl)-8-phenoxy-2,3-dihydro-1H-pyrrolo[3,2-c]-quinoline, 4-(3-benzylpyrrolidin-1-yl)-2-methyl-6-phenoxyquinoline, and N-[4-(3-benzylpyrrolidin-1-yl)-2-methylquinolin-6-yl]benzamide or a pharmaceutically acceptable derivative thereof, and an anesthetic agent or a pharmaceutically acceptable derivative thereof.

According to a further preferred embodiment of the invention there is provided the use of an antimicrobial agent selected from the group consisting of 4-methyl-1-(2-phenylethyl)-8-phenoxy-2,3-dihydro-1H-pyrrolo[3,2-c]-quinoline, 4-(3-benzyl pyrrolidin-1-yl)-2-methyl-6-phenoxyquinoline, and N-[4-(3-benzylpyrrolidin-1-yl)-2-methylquinolin-6-yl]benzamide or a pharmaceutically acceptable derivative thereof, in combination with an anesthetic agent or a pharmaceutically acceptable derivative thereof, for the manufacture of a medicament for the treatment of a microbial infection, in particular for killing multiplying and/or clinically latent microorganisms associated with such an infection.

There is also provided a method of treating a microbial infection, in particular killing multiplying and/or clinically latent microorganisms associated with such an infection, which comprises administering to a mammal, including man, an antimicrobial agent selected from the group consisting of 4-methyl-1-(2-phenylethyl)-8-phenoxy-2,3-dihydro-1H-pyrrolo[3,2-c]-quinoline, 4-(3-benzylpyrrolidin-1-yl)-2-methyl-6-phenoxyquinoline, and N-[4-(3-benzylpyrrolidin-1-yl)-2-methylquinolin-6-yl]benzamide or a pharmaceutically acceptable derivative thereof in combination with an anesthetic agent or a pharmaceutically acceptable derivative thereof.

There is further provided a pharmaceutical composition comprising an antimicrobial agent selected from the group consisting of 4-methyl-1-(2-phenylethyl)-8-phenoxy-2,3-dihydro-1H-pyrrolo[3,2-c]-quinoline, 4-(3-benzylpyrrolidin-1-yl)-2-methyl-6-phenoxyquinoline, and N-[4-(3-benzylpyrrolidin-1-yl)-2-methylquinolin-6-yl]benzamide or a pharmaceutically acceptable derivative thereof, an anesthetic agent or a pharmaceutically acceptable derivative thereof, and a pharmaceutically acceptable adjuvant, diluent or carrier; in particular for use in killing multiplying and/or clinically latent microorganisms associated with a microbial infection.

Compounds for use according to the invention may be administered simultaneously or sequentially and, when administered sequentially, either the antimicrobial agent having biological activity against clinically latent microorganisms or the anesthetic agent may be administered first. When administration is simultaneous, the combination may be administered either in the same or a different pharmaceutical composition.

According to a further embodiment of the invention, there is provided a product comprising an antimicrobial agent selected from the group consisting of 4-methyl-1-(2-phenylethyl)-8-phenoxy-2,3-dihydro-1H-pyrrolo[3,2-c]-quinoline, 4-(3-benzylpyrrolidin-1-yl)-2-methyl-6-phenoxyquinoline, and N-[4-(3-benzylpyrrolidin-1-yl)-2-methylquinolin-6-yl]benzamide or a pharmaceutically acceptable derivative thereof, and an anesthetic agent or a pharmaceutically acceptable derivative thereof as a combined preparation for simultaneous, separate or sequential use for the treatment of a microbial infection, in particular for killing log phase (multiplying) and/or clinically latent microorganisms associated with such an infection.

In a preferred embodiment of the invention, the antimicrobial agent is 4-methyl-1-(2-phenylethyl)-8-phenoxy-2,3-dihydro-1H-pyrrolo[3,2-c]-quinoline or a pharmaceutically acceptable derivative thereof, preferably the hydrochloride salt thereof, and the anesthetic agent is a local anesthetic, in particular dyclonine or a pharmaceutically acceptable derivative thereof, such as dyclonine hydrochloride.

In a further preferred embodiment of the invention, the antimicrobial agent is 4-(3-benzylpyrrolidin-1-yl)-2-methyl-6-phenoxyquinoline or N-[4-(3-benzylpyrrolidin-1-yl)-2-methylquinolin-6-yl]benzamide or a pharmaceutically acceptable derivative thereof, and the anesthetic agent is a local anesthetic, in particular dyclonine or a pharmaceutically acceptable derivative thereof, such as dyclonine hydrochloride.

In still a further preferred embodiment of the invention, the antimicrobial agent is mupirocin or a pharmaceutically acceptable derivative thereof, and the anesthetic agent is a local anesthetic, in particular dyclonine or a pharmaceutically acceptable derivative thereof, such as dyclonine hydrochloride.

Compounds for use according to the invention may be administered as the raw material but the active ingredients are preferably provided in the form of pharmaceutical compositions.

The active ingredients may be used either as separate formulations or as a single combined formulation. When combined in the same formulation it will be appreciated that the two compounds must be stable and compatible with each other and the other components of the formulation.

Formulations of the invention include those suitable for oral, parenteral (including subcutaneous e.g. by injection or by depot tablet, intradermal, intrathecal, intramuscular e.g. by depot and intravenous), rectal and topical (including dermal, buccal and sublingual) or in a form suitable for administration by inhalation or insufflation administration. The most suitable route of administration may depend upon the condition and disorder of the patient.

Preferably, the compositions of the invention are formulated for oral or topical administration. In a preferred embodiment, the composition is a cream or an ointment adapted for nasal administration, in particular for delivery to the anterior nares.

The formulations may conveniently be presented in unit dosage form and may be prepared by any of the methods well known in the art of pharmacy e.g. as described in "Remington: The Science and Practice of Pharmacy", Lippincott Williams and Wilkins, 21$^{st}$ Edition, (2005). Suitable methods include the step of bringing into association to active ingredients with a carrier which constitutes one or more excipients. In general, formulations are prepared by uniformly and intimately bringing into association the active ingredients with liquid carriers or finely divided solid carriers or both and then, if necessary, shaping the product into the desired formulation. It will be appreciated that when the two active ingredients are administered independently, each may be administered by a different means.

When formulated with excipients, the active ingredients may be present in a concentration from 0.1 to 99.5% (such as from 0.5 to 95%) by weight of the total mixture; conveniently from 30 to 95% for tablets and capsules and 0.01 to 50% (such as from 3 to 50%) for liquid preparations. A suitable concentration for 4-methyl-1-(2-phenylethyl)-8-phenoxy-2,3-dihydro-1H-pyrrolo[3,2-c]-quinoline or a pharmaceutically acceptable derivative thereof is from 0.1 to 5% (w/v) of the total mixture.

Formulations suitable for oral administration may be presented as discrete units such as capsules, cachets or tablets (e.g. chewable tablets in particular for paediatric administration), each containing a predetermined amount of active ingredient; as powder or granules; as a solution or suspension in an aqueous liquid or non-aqueous liquid; or as an oil-in-water liquid emulsion or water-in-oil liquid emulsion. The active ingredients may also be presented a bolus, electuary or paste.

A tablet may be made by compression or moulding, optionally with one or more excipients. Compressed tablets may be prepared by compressing in a suitable machine the active ingredient in a free-flowing form such as a powder or granules, optionally mixed with other conventional excipients such as binding agents (e.g. syrup, acacia, gelatin, sorbitol, tragacanth, mucilage of starch, polyvinylpyrrolidone and/or hydroxymethyl cellulose), fillers (e.g. lactose, sugar, microcrystalline cellulose, maize-starch, calcium phosphate and/or sorbitol), lubricants (e.g. magnesium stearate, stearic acid, talc, polyethylene glycol and/or silica), disintegrants (e.g. potato starch, croscarmellose sodium and/or sodium starch glycolate) and wetting agents (e.g. sodium lauryl sulphate). Moulded tablets may be made by moulding in a suitable machine a mixture of the powdered active ingredient with an inert liquid diluent. The tablets may be optionally coated or scored and may be formulated so as to provide controlled release (e.g. delayed, sustained, or pulsed release, or a combination of immediate release and controlled release) of the active ingredients.

Alternatively, the active ingredients may be incorporated into oral liquid preparations such as aqueous or oily suspensions, solutions, emulsions, syrups or elixirs. Formulations containing the active ingredients may also be presented as a dry product for constitution with water or another suitable vehicle before use. Such liquid preparations may contain conventional additives such as suspending agents (e.g. sorbitol syrup, methyl cellulose, glucose/sugar syrup, gelatin, hydroxymethyl cellulose, carboxymethyl cellulose, aluminium stearate gel and/or hydrogenated edible fats), emulsifying agents (e.g. lecithin, sorbitan mono-oleate and/or acacia), non-aqueous vehicles (e.g. edible oils, such as almond oil, fractionated coconut oil, oily esters, propylene glycol and/or ethyl alcohol), and preservatives (e.g. methyl or propyl p-hydroxybenzoates and/or sorbic acid).

Topical compositions, which are useful for treating disorders of the skin or of membranes accessible by digitation (such as membrane of the mouth, vagina, cervix, anus and rectum), include creams, ointments, lotions, sprays, gels and sterile aqueous solutions or suspensions. As such, topical compositions include those in which the active ingredients are dissolved or dispersed in a dermatological vehicle known in the art (e.g. aqueous or non-aqueous gels, ointments, water-in-oil or oil-in-water emulsions). Constituents of such vehicles may comprise water, aqueous buffer solutions, non-aqueous solvents (such as ethanol, isopropanol, benzyl alcohol, 2-(2-ethoxyethoxy)ethanol, propylene glycol, propylene glycol monolaurate, glycofurol or glycerol), oils (e.g. a mineral oil such as a liquid paraffin, natural or synthetic triglycerides such as Miglyol™, or silicone oils such as dimethicone). Depending, inter alia, upon the nature of the formulation as well as its intended use and site of application, the dermatological vehicle employed may contain one or more components selected from the following list: a solubilising agent or solvent (e.g. a β-cyclodextrin, such as hydroxypropyl β-cyclodextrin, or an alcohol or polyol such as ethanol, propylene glycol or glycerol); a thickening agent (e.g. hydroxymethyl cellulose, hydroxypropyl cellulose, carboxymethyl cellulose or carbomer); a gelling agent (e.g. a polyoxyethylene-polyoxypropylene copolymer); a preservative (e.g. benzyl alcohol, benzalkonium chloride, chlorhexidine, chlorbutol, a benzoate, potassium sorbate or EDTA or salt thereof); and pH buffering agent(s) (e.g. a mixture of dihydrogen phosphate and hydrogen phosphate salts, or a mixture of citric acid and a hydrogen phosphate salt). Topical formulations may also be formulated as a transdermal patch.

Methods of producing topical pharmaceutical compositions such as creams, ointments, lotions, sprays and sterile aqueous solutions or suspensions are well known in the art. Suitable methods of preparing topical pharmaceutical compositions are described, e.g. in WO9510999, U.S. Pat. No. 6,974,585, WO2006048747, as well as in documents cited in any of these references.

Topical pharmaceutical compositions according to the present invention may be used to treat a variety of skin or membrane disorders, such as infections of the skin or membranes (e.g. infections of nasal membranes, axilla, groin, perineum, rectum, dermatitic skin, skin ulcers, and sites of insertion of medical equipment such as i.v. needles, catheters and tracheostomy or feeding tubes) with any of the bacteria, fungi described above, (e.g. any of the Staphylococci, Streptococci, *Mycobacteria* or *Pseudomonas* organisms mentioned hereinbefore, such as *S. aureus* (e.g. Methicillin resistant *S. aureus* (MRSA))).

Particular bacterial conditions that may be treated by topical pharmaceutical compositions of the present invention also include the skin- and membrane-related conditions disclosed hereinbefore, as well as: acne vulgaris; rosacea (including erythematotelangiectatic rosacea, papulopustular rosacea, phymatous rosacea and ocular rosacea); erysipelas; erythrasma; ecthyma; ecthyma gangrenosum; impetigo; paronychia; cellulitis; folliculitis (including hot tub folliculitis); furunculosis; carbunculosis; staphylococcal scalded skin syndrome; surgical scarlet fever; streptococcal peri-anal disease; streptococcal toxic shock syndrome; pitted keratolysis; trichomycosis axillaris; pyoderma; external canal ear infections; green nail syndrome; spirochetes; necrotizing fasciitis; Mycobacterial skin infections (such as lupus vulgaris, scrofuloderma, warty tuberculosis, tuberculides, erythema nodosum, erythema induratum, cutaneous manifestations of tuberculoid leprosy or lepromatous leprosy, erythema nodosum leprosum, cutaneous *M. kansasii, M. malmoense, M. szulgai, M. simiae, M. gordonae, M. haemophilum, M. avium, M. intracellulare, M. chelonae* (including *M. abscessus*) or *M. fortuitum* infections, swimming pool (or fish tank) granuloma, lymphadenitis and Buruli ulcer (Bairnsdale ulcer, Searles' ulcer, Kakerifu ulcer or Toro ulcer)); as well as infected eczema, burns, abrasions and skin wounds.

Particular fungal conditions that may be treated by topical pharmaceutical compositions of the present invention also include the skin- and membrane-related conditions disclosed hereinbefore, as well as: candidiasis; sporotrichosis; ringworm (e.g. tinea pedis, tinea cruris, tinea capitis, tinea unguium or tinea corporis); tinea versicolor; and infections with *Trichophyton, Microsporum, Epidermophyton* or *Pityrosporum ovale* fungi.

Compositions for use according to the invention may be presented in a pack or dispenser device which may contain one or more unit dosage forms containing the active ingredients. The pack may, e.g. comprise metal or plastic foil, such as a blister pack. Where the compositions are intended for administration as two separate compositions these may be presented in the form of a twin pack.

Pharmaceutical compositions may also be prescribed to the patient in "patient packs" containing the whole course of treatment in a single package, usually a blister pack. Patient packs have an advantage over traditional prescriptions, where a pharmacist divides a patients' supply of a pharmaceutical from a bulk supply, in that the patient always has access to the package insert contained in the patient pack, normally missing in traditional prescriptions. The inclusion of the package insert has been shown to improve patient compliance with the physician's instructions.

The administration of the combination of the invention by means of a single patient pack, or patients packs of each composition, including a package insert directing the patient to the correct use of the invention is a desirable feature of this invention.

According to a further embodiment of the present invention there is provided a patient pack comprising at least one active ingredient of the combination according to the invention and an information insert containing directions on the use of the combination of the invention.

In another embodiment of the invention, there is provided a double pack comprising in association for separate administration, an antimicrobial agent, preferably having biological activity against clinically latent microorganisms, and an anesthetic agent, preferably having biological activity against clinically latent microorganisms.

The amount of active ingredients required for use in treatment will vary with the nature of the condition being treated and the age and condition of the patient, and will ultimately be at the discretion of the attendant physician or veterinarian. In general however, doses employed for adult human treatment will typically be in the range of 0.02 to 5000 mg per day, preferably 1 to 1500 mg per day. The desired dose may conveniently be presented in a single dose or as divided doses administered at appropriate intervals, e.g. as two, three, four or more sub-does per day.

Biological Tests

Test procedures that may be employed to determine the biological (e.g. bactericidal or antimicrobial) activity of the active ingredients include those known to persons skilled in the art for determining:

(a) bactericidal activity against clinically latent bacteria; and (b) antimicrobial activity against log phase bacteria.

In relation to (a) above, methods for determining activity against clinically latent bacteria include a determination, under conditions known to those skilled in the art (such as those described in *Nature Reviews, Drug Discovery* 1, 895-910 (2002), the disclosures of which are hereby incorporated by reference), of Minimum Stationary-cidal Concentration ("MSC") or Minimum Dormicidal Concentration ("MDC") for a test compound.

By way of example, WO2000028074 describes a suitable method of screening compounds to determine their ability to kill clinically latent microorganisms. A typical method may include the following steps:

(1) growing a bacterial culture to stationery phase;
(2) treating the stationary phase culture with one or more antimicrobial agents at a concentration and or time sufficient to kill growing bacteria, thereby selecting a phenotypically resistant sub-population;
(3) incubating a sample of the phenotypically resistant subpopulation with one or more test compounds or agents; and
(4) assessing any antimicrobial effects against the phenotypically resistant subpopulation.

According to this method, the phenotypically resistant sub-population may be seen as representative of clinically latent bacteria which remain metabolically active in vivo and which can result in relapse or onset of disease.

In relation to (b) above, methods for determining activity against log phase bacteria include a determination, under standard conditions (i.e. conditions known to those skilled in the art, such as those described in WO 2005014585, the disclosures of which document are hereby incorporated by reference), of Minimum Inhibitory Concentration ("MIC") or Minimum Bactericidal Concentration ("MBC") for a test compound. Specific examples of such methods are described below.

EXAMPLES

Example 1

In vitro efficacy test of dyclonine hydrochloride (HT00800059), 4-methyl-1-(2-phenylethyl)-8-phenoxy-2,3-dihydro-1H-pyrrolo[3,2-c]-quinoline (HT61) and both drugs in combination against stationary phase *Staphylococcus aureus*

Bacterial Strain

*Staphylococcus aureus* (Oxford); Gram positive; Reference strain.

Growth of Bacteria

Stationary phase growth of methicilin sensitive *Staphylococcus aureus* (MSSA) was carried out as follows:

Subculture of the bacterial strains on agar plates: Overnight *S. aureus* bacterial cultures were stored at −70° C. with 20% glycerol (cryoprotectant). A loopful of the frozen cells was streaked on a blood agar plate which was incubated at 37° C. overnight (or longer) as culture plate A. A single colony of each strain from the culture plate A was streaked on the blood agar plate which was incubated at 37° C. overnight (or longer) as culture plate B. The culture plate B was stored at 4° C. for a week and served as the initial inoculation plate.

Bacterial growth in broth culture: A single colony from culture plate B was inoculated in 10 ml of nutrient broth (No. 2, (Oxoid)), which was incubated overnight at 37° C. with continuous shaking at 120 rpm. 200 µl of the overnight culture was added into a 500 ml bottle containing 100 ml of nutrient broth. The 100 ml culture was incubated at 37° C. with continuous shaking for 6 to 7 days. Viability of the cultures is estimated by colony forming unit (CFU) counts at 2 hour intervals for the first 24 hours and 12 to 24 hours afterwards.

Colony Forming Unit (CFU) counts were performed as follows: From serial 10-fold dilutions of the cultures, 100 µl samples were added to one third of blood agar plates (Oxoid) in triplicate. CFUs were counted using an aCoLyte colony counter (Synbiosis) after incubation of the plates at 37° C. for 24 hours or longer.

Bacterial cultures: 10 µl of overnight cultures was added to 10 ml of fresh iso-sensitest broth to make the inoculation to $10^6$ CFU/ml. 290 µl of the cell suspension was added to each well of the 96 well plate, which was incubated at 37° C. for 24 hours. 300 µl of iso-sensitest broth without bacterial cells were added to wells of the plate as a no bacterial control.

MIC determination: The optical density of the bacterial cells was read at 405 nm using a plate reader (Bio TEK). The MIC concentration was determined as the lowest concentration of drug which inhibits the bacterial growth.

Drug Assay of Stationery Phase 7 day old stationary phase cultures were used. The stationary phase cultures were diluted to obtain CFU counts in the cell suspension of $10^6$ to $10^7$ CFU/ml. The cell suspension was used to test drug sensitivity.

Compounds and Preparation

HT61 was dissolved in DMSO to the stock concentration of 10 mg/ml.

HT00800059 was dissolved in $H_2O$ to the stock solution 10 mg/ml

The drugs were first diluted as follows:

7.2 µl of HT61 at 10 mg/ml was added into 292.8 µl of $H_2O$ followed by diluting 2 fold, 3 times.

57.6 µl of HT00800059 at 10 mg/ml was added into 242.4 µl of $H_2O$ followed by diluting 2 fold, 2 times.

10 µl of HT00800059 from each dilution was added into the wells of a 96 well plate followed by the addition of 290 µl of bacterial cell suspension to make the final concentrations of HT00800059 at 64, 32 and 0 µg/ml.

10 µl of HT00800059 from each dilution was added into the wells of a 96 well plate followed by the addition of 290 µl of bacterial cell suspension to make the final concentrations of HT00800059 at 64, 32 and 0 µg/ml.

In combination of two drugs: 10 μl of HT61 from each dilution was added into the wells of a 96 well plate followed by the addition of 10 μl of HT00800059 from each dilution. After addition of 280 μl of bacterial cell suspension to make the final concentrations of these two drugs as shown in the table below.

| HT61 (μg/ml) | HT00800059 (μg/ml) |
|---|---|
| 8 | 64 |
| 8 | 32 |
| 4 | 64 |
| 4 | 32 |
| 2 | 64 |
| 2 | 32 |

Incubation of the compounds with the bacterial suspension was carried out for 8 hours. CFU counts were carried out at 1 hour intervals.

Results

Figure 2:
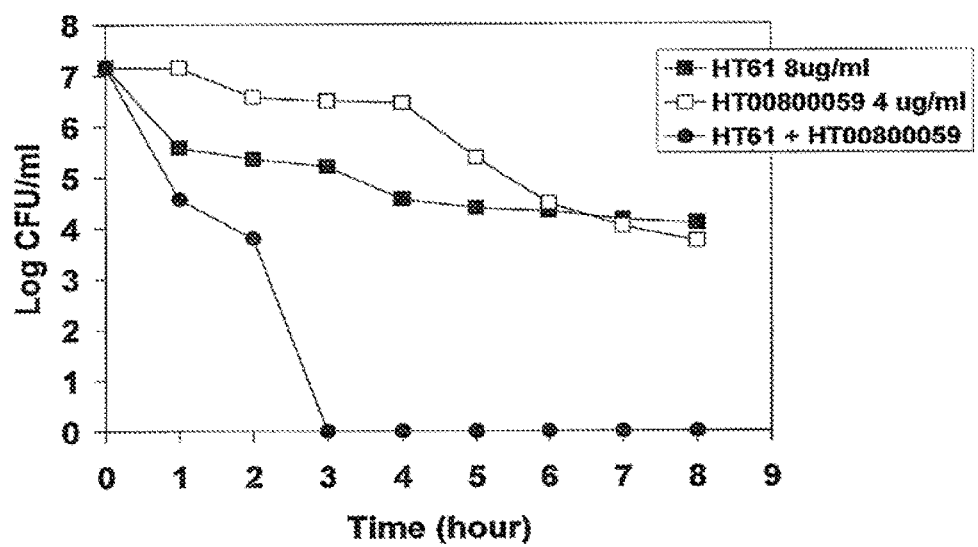
FIG. 2 shows an effect of HT61 and HT00800059 in combination against stationary phase *Staphylococcus aureus*.
Figure 3:
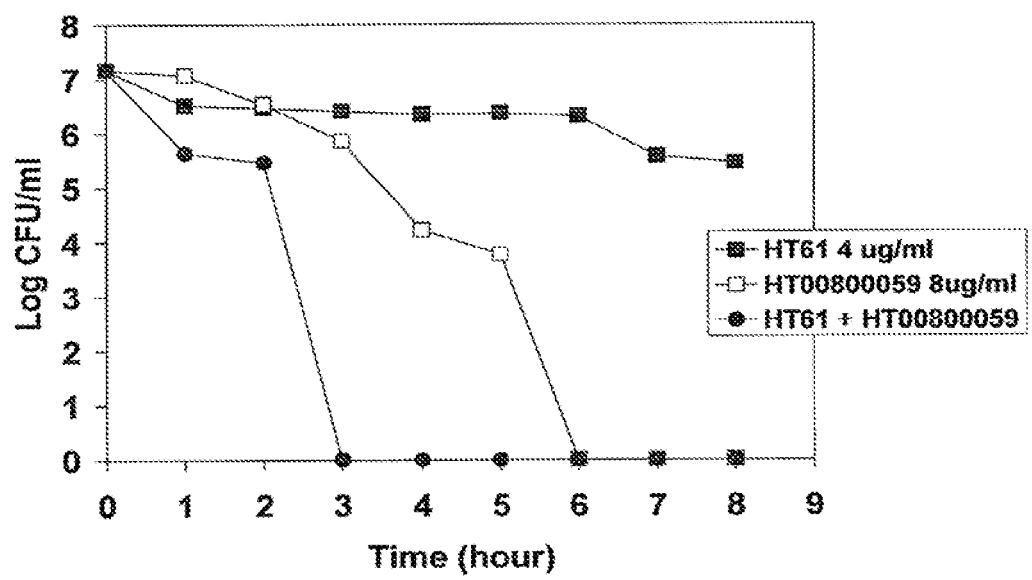
FIG. 3 shows an effect of HT61 and HT00800059 in combination against stationary phase *Staphylococcus aureus*.
Figure 4:
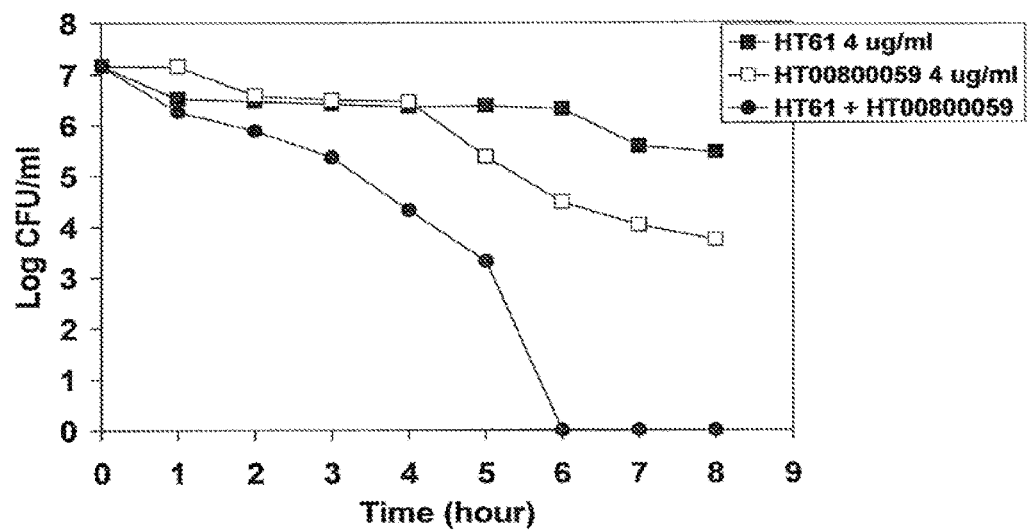
FIG. 4 shows an effect of HT61 and HT00800059 in combination against stationary phase *Staphylococcus aureus*.
Figure 5:
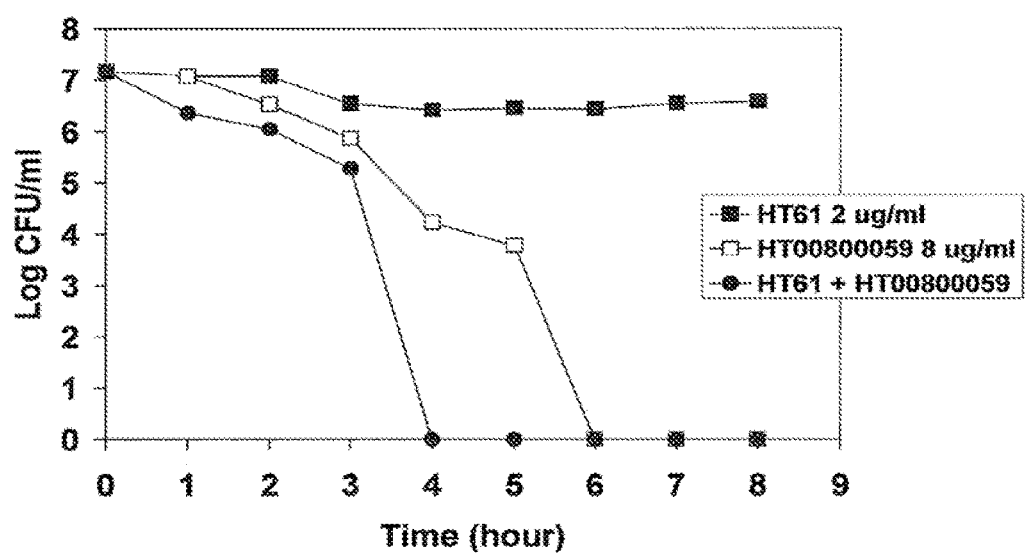
FIG. 5 shows an effect of HT61 and HT00800059 in combination against stationary phase *Staphylococcus aureus*.
Figure 6:
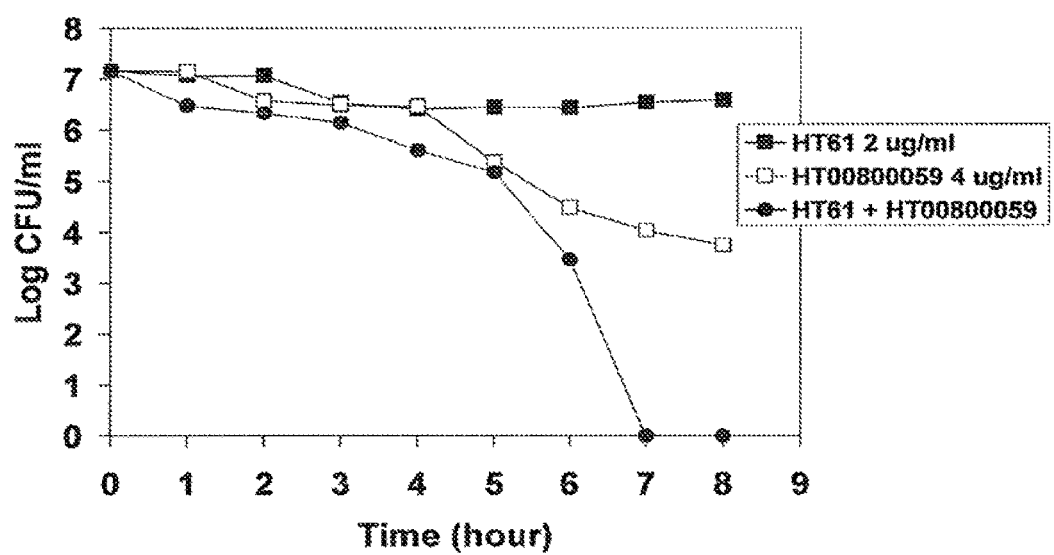
FIG. 6 shows an effect of HT61 and HT00800059 in combination against stationary phase *Staphylococcus aureus*.

The results of these experiments are summarised in FIGS. 1 to 6.

Conclusions

1. HT61 at a concentration of 8 μg/ml exhibited low activity against stationary phase *S. aureus*.
2. HT61 at concentrations of 4 and 2 μg/ml exhibited no observed activity against stationary phase *S. aureus*.
3. HT00800059 at a concentration of 64 μg/ml killed about $10^7$ CFU over 6 hours.
4. HT00800059 at a concentration of 32 μg/ml killed about $10^4$ CFU over 8 hours.
5. HT61 in combination with HT00800059 exhibited synergistic activity against stationary phase *S. aureus*.

Example 2

In Vitro Activity of HT00800059, HT61 and Both Drugs in Combination Against Log Phase *Staphylococcus aureus* by Chequerboard Analysis Bacterial Strain

*Staphylococcus aureus* (Oxford); Gram positive; Reference strain.

Growth of Bacteria

Log phase growth of methicilin sensitive *Staphylococcus aureus* (MSSA) was carried out as follows:

Bacteria were grown in 10 ml of nutrient broth (No. 2, (Oxoid)) overnight at 37° C. with continuous shaking at 120 rpm. The overnight cultures were diluted 1000× with iso-sensitest broth. The cultures were incubated at 37° C. with shaking for 1-2 hours to reach log CFU 6. Viability of the bacteria was estimated by colony forming unit (CFU) counts. From serial 10-fold dilutions of the experimental cultures, 100 μl samples were added to triplicate plates of nutrient agar plates (Oxoid) or blood agar plates (Oxoid). CFUs were counted after incubation of the plates at 37° C. for 24 hours.

Bacterial cultures: 10 μl of overnight cultures was added to 10 ml of fresh iso-sensitest broth to make the inoculation to $10^6$ CFU/ml. 290 μl of the cell suspension was added to each well of the 96 well plate, which was incubated at 37° C. for 24 hours. 300 μl of iso-sensitest broth without bacterial cells were added to wells of the plate as a no bacterial control.

MIC determination: The optical density of the bacterial cells was read at 405 nm using a plate reader (Bio TEK). The MIC concentration was determined as the lowest concentration of drug which inhibits the bacterial growth.

Compounds and Preparation

HT61 was dissolved in DMSO to the stock concentration of 10 mg/ml.

HT00800059 was dissolved in $H_2O$ to the stock solution 30.07 mg/ml.

The drugs were first diluted as follows:

28.8 μl of HT61 at 10 mg/ml was added into 271.2 μl of $H_2O$ followed by diluting 2 fold for 6 times.

HT00800059 at 30.07 mg/ml was diluted 2 fold for 11 times.

Both drugs were mixed as following pattern: 10 μl of HT00800059 from each dilution was added into the wells of a 96 well plate from top to bottom and 10 μl of HT61 from each dilution was added to the same 96 well plate from left to right. After addition of 280 μl log phase cell suspension, the final concentrations of drugs for each well in the 96 well plate are shown in the table below.

| | 1 | 2 | 3 | 4 | 5 | 6 | 7 | 8 | 9 | 10 | 11 | 12 | |
|---|---|---|---|---|---|---|---|---|---|---|---|---|---|
| HT00800059 | 1024 | 512 | 256 | 128 | 64 | 32 | 16 | 8 | 4 | 2 | 1 | 0 | A |
| HT61 | 32 | 32 | 32 | 32 | 32 | 32 | 32 | 32 | 32 | 32 | 32 | 32 | |
| HT00800059 | 1024 | 512 | 256 | 128 | 64 | 32 | 16 | 8 | 4 | 2 | 1 | 0 | B |
| HT61 | 16 | 16 | 16 | 16 | 16 | 16 | 16 | 16 | 16 | 16 | 16 | 16 | |
| HT00800059 | 1024 | 512 | 256 | 128 | 64 | 32 | 16 | 8 | 4 | 2 | 1 | 0 | C |
| HT61 | 8 | 8 | 8 | 8 | 8 | 8 | 8 | 8 | 8 | 8 | 8 | 8 | |
| HT00800059 | 1024 | 512 | 256 | 128 | 64 | 32 | 16 | 8 | 4 | 2 | 1 | 0 | D |
| HT61 | 4 | 4 | 4 | 4 | 4 | 4 | 4 | 4 | 4 | 4 | 4 | 4 | |
| HT00800059 | 1024 | 512 | 256 | 128 | 64 | 32 | 16 | 8 | 4 | 2 | 1 | 0 | E |
| HT61 | 2 | 2 | 2 | 2 | 2 | 2 | 2 | 2 | 2 | 2 | 2 | 2 | |
| HT00800059 | 1024 | 512 | 256 | 128 | 64 | 32 | 16 | 8 | 4 | 2 | 1 | 0 | F |
| HT61 | 1 | 1 | 1 | 1 | 1 | 1 | 1 | 1 | 1 | 1 | 1 | 1 | |
| HT00800059 | 1024 | 512 | 256 | 128 | 64 | 32 | 16 | 8 | 4 | 2 | 1 | 0 | G |
| HT61 | 0.5 | 0.5 | 0.5 | 0.5 | 0.5 | 0.5 | 0.5 | 0.5 | 0.5 | 0.5 | 0.5 | 0.5 | |
| HT00800059 | 1024 | 512 | 256 | 128 | 64 | 32 | 16 | 8 | 4 | 2 | 1 | 0 | H |
| HT61 | 0 | 0 | 0 | 0 | 0 | 0 | 0 | 0 | 0 | 0 | 0 | 0 | |

Incubation of the compounds with the bacterial suspension was carried out for 24 hours. The kill effect of the drug combination and signal drug MIC was measured by optical density reading at 405 nm with a plate reader (Bio TEK). The MIC concentration was determined as the lowest concentration of drug which inhibits the bacterial growth.

The fractional inhibitory concentration (FIC) index was carried out as follows: (MIC of drug A, tested in combination)/(MIC of drug A, tested alone)+(MIC of drug B, tested in combination)/(MIC of drug B, tested alone). The interaction was defined as synergistic if the FIC index was <1, additive if the FIC index was =1 and antagonistic if the FIC index was >1.

Results

Conclusion

The FIC for HT61 in combination with HT00800059 was 0/5, which is indicative of a synergistic effect against log phase *Staphylococcus aureus*.

Example 3
In vitro activity of dyclonine hydrochloride (HT00800059), 4-(3-benzylpyrrolidin-1-yl)-2-methyl-6-phenoxyquinoline (HT230) and N-[4-(3-benzylpyrrolidin-1-yl)-2-methylquinolin-6-yl]benzamide (HT281), and combinations thereof, against log phase *Staphylococcus aureus* by chequerboard analysis Bacterial Strain

*Staphylococcus aureus* (Oxford); Gram positive; Reference strain.

Plate 1

HT00800059 →

| HT61 | 1024 | 512 | 256 | 128 | 64 | 32 | 16 | 8 | 4 | 2 | 1 | 0 |
|---|---|---|---|---|---|---|---|---|---|---|---|---|
| 32 | 0.615 | 0.629 | 0.526 | 0.506 | 0.506 | 0.503 | 0.504 | 0.501 | 0.499 | 0.505 | 0.505 | 0.502 |
| 16 | 0.396 | 0.377 | 0.374 | 0.375 | 0.372 | 0.373 | 0.374 | 0.372 | 0.372 | 0.375 | 0.372 | 0.371 |
| 8 | 0.374 | 0.369 | 0.367 | 0.368 | 0.367 | 0.366 | 0.367 | 0.366 | 0.366 | 0.370 | 0.367 | 0.367 |
| 4 | 0.365 | 0.365 | 0.365 | 0.377 | 0.598 | 0.687 | 0.712 | 0.855 | 0.798 | 0.927 | 0.802 | 0.780 |
| 2 | 0.363 | 0.365 | 0.453 | 0.790 | 0.897 | 0.845 | 0.920 | 0.908 | 0.925 | 1.050 | 0.915 | 0.858 |
| 1 | 0.364 | 0.364 | 0.664 | 0.812 | 0.825 | 0.948 | 0.886 | 0.998 | 0.963 | 0.945 | 0.929 | 0.907 |
| 0.5 | 0.362 | 0.362 | 0.616 | 0.683 | 0.914 | 0.836 | 0.858 | 0.905 | 0.959 | 0.795 | 0.817 | 0.943 |
| 0 | 0.360 | 0.360 | 0.548 | 0.816 | 0.942 | 0.949 | 1.024 | 0.949 | 0.945 | 0.924 | 0.899 | 0.967 |

MIC  HT00800059              512.000
     HT00800059 + HT61  4 µg/ml  128.000
     HT61                      8.000
     HT61 + HT00800059  128 µg/ml  4.000
FIC  0.75

Plate 2

HT00800059 →

| HT61 | 1024 | 512 | 256 | 128 | 64 | 32 | 16 | 8 | 4 | 2 | 1 | 0 |
|---|---|---|---|---|---|---|---|---|---|---|---|---|
| 32 | 0.593 | 0.576 | 0.506 | 0.480 | 0.485 | 0.473 | 0.478 | 0.504 | 0.478 | 0.494 | 0.485 | 0.480 |
| 16 | 0.404 | 0.380 | 0.379 | 0.376 | 0.378 | 0.379 | 0.375 | 0.378 | 0.375 | 0.378 | 0.379 | 0.380 |
| 8 | 0.380 | 0.371 | 0.371 | 0.370 | 0.372 | 0.372 | 0.370 | 0.372 | 0.370 | 0.369 | 0.372 | 0.370 |
| 4 | 0.369 | 0.363 | 0.367 | 0.378 | 0.554 | 0.634 | 0.637 | 0.704 | 0.717 | 0.735 | 0.796 | 0.859 |
| 2 | 0.369 | 0.366 | 0.445 | 0.831 | 0.936 | 0.866 | 0.891 | 0.943 | 1.008 | 0.873 | 0.884 | 0.930 |
| 1 | 0.370 | 0.364 | 0.636 | 0.782 | 0.906 | 0.954 | 0.961 | 0.948 | 0.975 | 0.959 | 0.916 | 0.881 |
| 0.5 | 0.369 | 0.364 | 0.668 | 0.769 | 0.816 | 0.905 | 0.909 | 0.883 | 0.887 | 0.887 | 0.868 | 0.850 |
| 0 | 0.367 | 0.364 | 0.616 | 0.831 | 0.890 | 0.845 | 0.839 | 0.812 | 0.834 | 0.865 | 0.861 | 0.893 |

FIC = 0.75
MIC  HT00800059              512
     HT00800059 + HT61  4 µg/ml  128
     HT61                      8
     HT61 + HT00800059  128 µg/ml  4

1. HT61 alone MIC 16 µg/ml.
2. HT00800059 alone MIC 512 µg/ml.
3. With HT61 4 µg/ml, HT00800059 MIC reduced to 128 µg/ml.
4. With HT00800059 at 128 µg/ml, HT61 MIC reduced to 8 µg/ml.

Growth of Bacteria

Log phase growth of methicilin sensitive *Staphylococcus aureus* (MSSA) was carried out as follows:

Bacteria were grown in 10 ml of nutrient broth (No. 2, (Oxoid)) overnight at 37° C. with continuous shaking at 120 rpm. The overnight cultures were diluted 1000× with iso-sensitest broth. The cultures were incubated at 37° C. with shaking for 1-2 hours to reach log CFU 6. Viability of the bacteria was estimated by colony forming unit (CFU) counts. From serial 10-fold dilutions of the experimental cultures, 100 μl samples were added to triplicate plates of nutrient agar plates (Oxoid) or blood agar plates (Oxoid). CFUs were counted after incubation of the plates at 37° C. for 24 hours.

Bacterial cultures: 10 μl of overnight cultures was added to 10 ml of fresh iso-sensitest broth to make the inoculation to $10^6$ CFU/ml. 290 μl of the cell suspension was added to each well of the 96 well plate, which was incubated at 37° C. for 24 hours. 300 μl of iso-sensitest broth without bacterial cells were added to wells of the plate as a no bacterial control.

MIC determination: The optical density of the bacterial cells was read at 405 nm using a plate reader (Bio TEK). The MIC concentration was determined as the lowest concentration of drug which inhibits the bacterial growth.

In the above table, values in bold text are for HT00800059. Values in plain text are for HT230 or HT281. The numbers shown in each well are μg/ml.

Incubation of the compounds with the bacterial suspension was carried out for 24 hours. The kill effects of the drug combination were measured by optical density reading at 405 nm with a plate reader (Bio TEK).

Chequerboard Analysis

The fractional inhibitory concentration (FIC) index was carried out as follows: (MIC of drug A, tested in combination)/(MIC of drug A, tested alone)+(MIC of drug B, tested in combination)/(MIC of drug B, tested alone). The interaction was defined as synergistic if the FIC index was <1, additive if the FIC index was =1 and antagonistic if the FIC index was >1.

Results (1) HT230

Chequerboard Analysis of Synergistic Effect Between HT230 and HT00800059:

| HT00800059 | HT230 32 | 16 | 8 | 4 | 2 | 1 | 0.5 | 0.25 | 0.125 | 0.0625 | 0.03125 | 0 |
|---|---|---|---|---|---|---|---|---|---|---|---|---|
| 1024 | 0.658 | 0.471 | 0.396 | 0.370 | 0.365 | 0.363 | 0.363 | 0.364 | 0.367 | 0.362 | 0.361 | 0.367 |
| 512 | 0.520 | 0.385 | 0.364 | 0.363 | 0.363 | 0.362 | 0.361 | 0.366 | 0.363 | 0.364 | 0.367 | 0.366 |
| 256 | 0.457 | 0.374 | 0.361 | 0.362 | 0.358 | 0.371 | 0.859 | 0.888 | 0.787 | 0.840 | 1.063 | 0.736 |
| 128 | 0.429 | 0.365 | 0.359 | 0.362 | 0.362 | 1.040 | 1.040 | 1.106 | 1.108 | 1.188 | 1.129 | 1.210 |
| 64 | 0.419 | 0.362 | 0.358 | 0.356 | 0.382 | 1.121 | 1.114 | 1.101 | 1.104 | 1.058 | 1.071 | 1.139 |
| 32 | 0.418 | 0.362 | 0.360 | 0.357 | 1.000 | 1.149 | 1.144 | 1.084 | 1.074 | 1.114 | 1.120 | 1.235 |
| 16 | 0.418 | 0.360 | 0.357 | 0.359 | 1.025 | 1.106 | 1.074 | 1.098 | 1.088 | 1.204 | 1.151 | 1.282 |
| 0 | 0.406 | 0.357 | 0.363 | 0.365 | 1.190 | 1.160 | 1.135 | 1.401 | 1.317 | 1.312 | 1.237 | 1.230 |

Compounds and Preparation

HT230 was dissolved in DMSO to the stock concentration of 10 mg/ml.

HT281 was dissolved in DMSO to the stock concentration of 10 mg/ml.

HT00800059 was dissolved in $H_2O$ to the stock solution 30.07 mg/ml.

HT230 or HT281 (10 mg/ml) was firstly diluted to 0.96 mg/ml, then a serial of 2 fold dilution was carried out.

HT00800059 (30.7 mg/ml) was diluted in a serial of 2 fold.

10 μl from each dilution of each drug was added to the 96 well plates in a two dimensional array shown in the table below. This was followed by the addition of 280 μl of log phase culture at $10^6$ CFU/ml to make the final concentrations of each drug as shown.

Combination of HT230 or HT281 with HT00800059:

Values in bold text represent growth. MIC: HT00800059 before combination was 512 and after combination was 64; HT230 before combination was 4 and after combination was 1. FIC: 64/512+1/4=0.375.

(2) HT281

Chequerboard Analysis of Synergistic Effect Between HT281 and HT00800059:

| 1024 | 1024 | 1024 | 1024 | 1024 | 1024 | 1024 | 1024 | 1024 | 1024 | 1024 | 1024 |
|---|---|---|---|---|---|---|---|---|---|---|---|
| 32 | 16 | 8 | 4 | 2 | 1 | 0.5 | 0.25 | 0.125 | 0.0625 | 0.03125 | 0 |
| 512 | 512 | 512 | 512 | 512 | 512 | 512 | 512 | 512 | 512 | 512 | 512 |
| 32 | 16 | 8 | 4 | 2 | 1 | 0.5 | 0.25 | 0.125 | 0.0625 | 0.03125 | 0 |
| 256 | 256 | 256 | 256 | 256 | 256 | 256 | 256 | 256 | 256 | 256 | 256 |
| 32 | 16 | 8 | 4 | 2 | 1 | 0.5 | 0.25 | 0.125 | 0.0625 | 0.03125 | 0 |
| 128 | 128 | 128 | 128 | 128 | 128 | 128 | 128 | 128 | 128 | 128 | 128 |
| 32 | 16 | 8 | 4 | 2 | 1 | 0.5 | 0.25 | 0.125 | 0.0625 | 0.03125 | 0 |
| 64 | 64 | 64 | 64 | 64 | 64 | 64 | 64 | 64 | 64 | 64 | 64 |
| 32 | 16 | 8 | 4 | 2 | 1 | 0.5 | 0.25 | 0.125 | 0.0625 | 0.03125 | 0 |
| 32 | 32 | 32 | 32 | 32 | 32 | 32 | 32 | 32 | 32 | 32 | 32 |
| 32 | 16 | 8 | 4 | 2 | 1 | 0.5 | 0.25 | 0.125 | 0.0625 | 0.03125 | 0 |
| 16 | 16 | 16 | 16 | 16 | 16 | 16 | 16 | 16 | 16 | 16 | 16 |
| 32 | 16 | 8 | 4 | 2 | 1 | 0.5 | 0.25 | 0.125 | 0.0625 | 0.03125 | 0 |
| 0 | 0 | 0 | 0 | 0 | 0 | 0 | 0 | 0 | 0 | 0 | 0 |
| 32 | 16 | 8 | 4 | 2 | 1 | 0.5 | 0.25 | 0.125 | 0.0625 | 0.03125 | 0 |

| HT00800059 | 64 | 32 | 16 | 8 | 4 | HT281 2 | 1 | 0.5 | 0.25 | 0.125 | 0.625 | 0 |
|---|---|---|---|---|---|---|---|---|---|---|---|---|
| 1024 | 0.668 | 0.517 | 0.425 | 0.388 | 0.370 | 0.365 | 0.368 | 0.364 | 0.363 | 0.369 | 0.366 | 0.370 |
| 512 | 0.578 | 0.428 | 0.377 | 0.367 | 0.368 | 0.362 | 0.368 | 0.370 | 0.390 | 0.372 | 0.366 | 0.368 |
| 256 | 0.575 | 0.410 | 0.371 | 0.365 | 0.367 | 0.728 | 0.801 | 0.816 | 0.673 | 0.611 | 0.537 | 0.543 |
| 128 | 0.558 | 0.401 | 0.367 | 0.364 | 0.364 | 1.114 | 1.089 | 1.140 | 1.158 | 1.183 | 1.151 | 1.103 |
| 64 | 0.561 | 0.398 | 0.366 | 0.363 | 0.724 | 1.090 | 1.061 | 1.086 | 1.057 | 1.093 | 1.051 | 1.115 |
| 32 | 0.564 | 0.396 | 0.367 | 0.361 | 0.382 | 1.046 | 1.073 | 1.093 | 1.121 | 1.154 | 1.156 | 1.201 |
| 16 | 0.560 | 0.395 | 0.362 | 0.356 | 0.676 | 1.067 | 1.139 | 1.242 | 1.359 | 1.378 | 1.340 | 1.326 |
| 0 | 0.558 | 0.396 | 0.364 | 0.361 | 1.080 | 1.157 | 1.263 | 1.378 | 1.281 | 1.334 | 1.256 | 1.266 |

Values in bold text represent growth. MIC: HT00800059 before combination was 512 and after combination was 128. HT281 before combination was 8 and after combination was 4. FIC: $128/512 + 4/8 = 0.75$.

1. HT230 alone MIC 4 µg/ml.
2. HT00800059 alone MIC 512 µg/ml.
3. With HT230 at 2 µg/ml, HT00800059 MIC reduced to 64 µg/ml.
4. With HT00800059 at 256 µg/ml, HT230 MIC reduced to 1 µg/ml.
5. HT281 alone MIC 8 µg/ml.
6. With HT281 at 4 µg/ml, HT00800059 MIC reduced to 128 µg/ml.
7. With HT00800059 at 128 µg/ml, HT230 MIC reduced to 4 µg/ml.

Conclusions

The FIC for HT230 in combination with HT00800059 was 0.375, which is indicative of a synergistic effect against log phase *Staphylococcus aureus*.

The FIC for HT281 in combination with HT00800059 was 0.75, which is indicative of a synergistic effect against log phase *Staphylococcus aureus*.

Example 4

In Vitro Activity of Dyclonine Hydrochloride (HT00800059), Mupirocin and Both Drugs in Combination Against Log Phase *Staphylococcus aureus* by Chequerboard Analysis Bacterial Strain

*Staphylococcus aureus* (Oxford); Gram positive; Reference strain.

Growth of Bacteria

Log phase growth of methicilin sensitive *Staphylococcus aureus* (MSSA) was carried out as follows:

Bacteria were grown in 10 ml of nutrient broth (No. 2, (Oxoid)) overnight at 37° C. with continuous shaking at 120 rpm. The overnight cultures were diluted 1000× with iso-sensitest broth. The cultures were incubated at 37° C. with shaking for 1-2 hours to reach log CFU 6. Viability of the bacteria was estimated by colony forming unit (CFU) counts. From serial 10-fold dilutions of the experimental cultures, 100 µl samples were added to triplicate plates of nutrient agar plates (Oxoid) or blood agar plates (Oxoid). CFUs were counted after incubation of the plates at 37° C. for 24 hours.

Bacterial cultures: 10 µl of overnight cultures was added to 10 ml of fresh iso-sensitest broth to make the inoculation to $10^6$ CFU/ml. 290 µl of the cell suspension was added to each well of the 96 well plate, which was incubated at 37° C. for 24 hours. 300 µl of iso-sensitest broth without bacterial cells were added to wells of the plate as a no bacterial control.

MIC determination: The optical density of the bacterial cells was read at 405 nm using a plate reader (Bio TEK). The MIC concentration was determined as the lowest concentration of drug which inhibits the bacterial growth.

Compounds and Preparation

Mupirocin was dissolved in DMSO to the stock concentration of 10 mg/ml, then diluted 10 fold with DMSO to 1 mg/ml.

HT00800059 was dissolved in $H_2O$ to the stock solution 30.07 mg/ml.

Mupirocin (1 mg/ml) was performed in a serial of 2 fold dilutions.

HT00800059 (30.7 mg/ml) was performed in a serial of 2 fold dilutions.

10 µl of each dilution from each drug was added to the 96 well plates in a two dementional array as shown in the table below. This was followed by the addition of 280 µl of log phase culture at $10^6$ CFU/ml to make the final concentrations of each drug as shown.

Combination of Mupirocin with HT00800059:

| 1024 | 512 | 256 | 128 | 64 | 32 | 16 | 8 | 4 | 2 | 1 | 0 |
|---|---|---|---|---|---|---|---|---|---|---|---|
| 1 | 1 | 1 | 1 | 1 | 1 | 1 | 1 | 1 | 1 | 1 | 1 |
| 1024 | 512 | 256 | 128 | 64 | 32 | 16 | 8 | 4 | 2 | 1 | 0 |
| 0.5 | 0.5 | 0.5 | 0.5 | 0.5 | 0.5 | 0.5 | 0.5 | 0.5 | 0.5 | 0.5 | 0.5 |
| 1024 | 512 | 256 | 128 | 64 | 32 | 16 | 8 | 4 | 2 | 1 | 0 |
| 0.25 | 0.25 | 0.25 | 0.25 | 0.25 | 0.25 | 0.25 | 0.25 | 0.25 | 0.25 | 0.25 | 0.25 |
| 1024 | 512 | 256 | 128 | 64 | 32 | 16 | 8 | 4 | 2 | 1 | 0 |
| 0.125 | 0.125 | 0.125 | 0.125 | 0.125 | 0.125 | 0.125 | 0.125 | 0.125 | 0.125 | 0.125 | 0.125 |
| 1024 | 512 | 256 | 128 | 64 | 32 | 16 | 8 | 4 | 2 | 1 | 0 |
| 0.0625 | 0.0625 | 0.0625 | 0.0625 | 0.0625 | 0.0625 | 0.0625 | 0.0625 | 0.0625 | 0.0625 | 0.0625 | 0.0625 |
| 1024 | 512 | 256 | 128 | 64 | 32 | 16 | 8 | 4 | 2 | 1 | 0 |
| 0.0313 | 0.0313 | 0.0313 | 0.0313 | 0.0313 | 0.0313 | 0.0313 | 0.0313 | 0.0313 | 0.0313 | 0.0313 | 0.0313 |
| 1024 | 512 | 256 | 128 | 64 | 32 | 16 | 8 | 4 | 2 | 1 | 0 |
| 0.0156 | 0.0156 | 0.0156 | 0.0156 | 0.0156 | 0.0156 | 0.0156 | 0.0156 | 0.0156 | 0.0156 | 0.0156 | 0.0156 |
| 1024 | 512 | 256 | 128 | 64 | 32 | 16 | 8 | 4 | 2 | 1 | 0 |
| 0 | 0 | 0 | 0 | 0 | 0 | 0 | 0 | 0 | 0 | 0 | 0 |

In the above table, values in bold text are for HT00800059. Values in plain text are for mupirocin. The numbers shown in each well are μg/ml.

Incubation of the compounds with the bacterial suspension was carried out for 24 hours. The kill effects of the drug combination were measured by optical density reading at 405 nm with a plate reader (Bio TEK).

Chequerboard Analysis

The fractional inhibitory concentration (FIC) index was carried out as following: (MIC of drug A, tested in combination)/(MIC of drug A, tested alone)+(MIC of drug B, tested in combination)/(MIC of drug B, tested alone). The interaction was defined as synergistic if the FIC index was <1, additive if the FIC index was =1 and antagonistic if the FIC index was >1.

Results (1) HT0080059

Chequerboard Analysis of Synergistic Effect Between Mupirocin and HT00800059 Using Nutrient Broth

|  |  | HT00800059 | | | | | | | | | | | |
| --- | --- | --- | --- | --- | --- | --- | --- | --- | --- | --- | --- | --- | --- |
|  |  | 1024 | 512 | 256 | 128 | 64 | 32 | 16 | 8 | 4 | 2 | 1 | 0 |
| Mupirocin | 1 | 0.292 | 0.288 | 0.289 | 0.287 | 0.295 | 0.299 | 0.302 | 0.299 | 0.296 | 0.297 | 0.293 | 0.290 |
|  | 0.5 | 0.289 | 0.290 | 0.292 | 0.294 | 0.302 | 0.299 | 0.300 | 0.302 | 0.298 | 0.301 | 0.296 | 0.296 |
|  | 0.25 | 0.291 | 0.288 | 0.290 | 0.290 | 0.300 | 0.300 | 0.312 | 0.315 | 0.315 | 0.329 | 0.320 | 0.328 |
|  | 0.125 | 0.289 | 0.288 | 0.290 | 0.297 | 0.340 | 0.375 | 0.406 | 0.410 | 0.403 | 0.410 | 0.409 | 0.487 |
|  | 0.625 | 0.290 | 0.287 | 0.291 | 0.344 | 0.500 | 0.643 | 0.717 | 0.717 | 0.744 | 0.804 | 0.725 | 0.816 |
|  | 0.03125 | 0.292 | 0.290 | 0.570 | 0.635 | 0.733 | 0.806 | 0.814 | 0.865 | 0.849 | 0.869 | 0.867 | 0.910 |
|  | 0.15625 | 0.292 | 0.289 | 0.535 | 0.572 | 0.677 | 0.785 | 0.789 | 0.828 | 0.802 | 0.815 | 0.854 | 0.936 |
|  | 0 | 0.291 | 0.284 | 0.524 | 0.528 | 0.721 | 0.759 | 0.840 | 0.867 | 0.885 | 0.884 | 0.858 | 0.973 |

Values in bold text represent growth. MIC: HT00800059 before combination was 512 and post combination was 64. Mupirocin before combination was 0.25 and post combination was 0.0625. FIC: 64/512+0.0625/0.25=0.375.

Chequerboard Analysis of Synergistic Effect Between Mupirocin and HT00800059 Using Iso-Sensitest Broth

|  |  | HT00800059 | | | | | | | | | | | |
| --- | --- | --- | --- | --- | --- | --- | --- | --- | --- | --- | --- | --- | --- |
|  |  | 1024 | 512 | 256 | 128 | 64 | 32 | 16 | 8 | 4 | 2 | 1 | 0 |
| Mupirocin | 1 | 0.35 | 0.36 | 0.37 | 0.36 | 0.36 | 0.37 | 0.36 | 0.37 | 0.36 | 0.36 | 0.37 | 0.37 |
|  | 0.5 | 0.36 | 0.36 | 0.37 | 0.36 | 0.37 | 0.40 | 0.36 | 0.37 | 0.37 | 0.42 | 0.37 | 0.37 |
|  | 0.25 | 0.36 | 0.36 | 0.36 | 0.36 | 0.37 | 0.37 | 0.37 | 0.38 | 0.38 | 0.39 | 0.37 | 0.39 |
|  | 0.125 | 0.36 | 0.36 | 0.36 | 0.37 | 0.40 | 0.44 | 0.45 | 0.45 | 0.47 | 0.48 | 0.46 | 0.48 |
|  | 0.0625 | 0.36 | 0.36 | 0.36 | 0.49 | 0.59 | 0.64 | 0.66 | 0.66 | 0.65 | 0.67 | 0.68 | 0.73 |
|  | 0.03125 | 0.36 | 0.36 | 0.58 | 0.70 | 0.76 | 0.81 | 0.85 | 0.84 | 0.84 | 0.83 | 0.85 | 0.82 |
|  | 0.015625 | 0.36 | 0.36 | 0.82 | 1.06 | 0.97 | 1.08 | 1.06 | 1.05 | 1.02 | 1.03 | 1.05 | 1.00 |
|  | 0 | 0.36 | 0.36 | 1.09 | 1.20 | 1.34 | 1.55 | 1.52 | 1.47 | 1.46 | 1.47 | 1.49 | 1.45 |

Values in bold text represent growth. MIC: HT00800059 before combination was 512 and post combination was 64. Mupirocin before combination was 0.25 and post combination was 0.0625. FIC: 64/512+0.0625/0.25=0.375.

1. Mupriocin alone MIC 0.25 μg/ml.
2. HT00800059 alone MIC 512 μg/ml.
3. With mupirocin 0.125 μg/ml, HT00800059 MIC reduced to 64 μg/ml.
4. With HT00800059 at 256 μg/ml, mupirocin MIC reduced to 0.0625 μg/ml.

Conclusion

The FIC for mupirocin in combination with HT00800059 was 0.375, which is indicative of a synergistic effect against log phase *Staphylococcus aureus*. The results were reproducible using two different broths.

Example 5

In Vitro Activity of Dyclonine Hydrochloride (HT00800059), Mupirocin and Both Drugs in Combination Against Log Phase Mupirocin Resistant *Staphylococcus aureus* by Chequerboard Analysis Bacterial Strain

*Staphylococcus aureus* (Oxford); Gram positive; Reference strain.

Growth of Bacteria

Log phase growth of mupirocin resistant *Staphylococcus aureus* (MSSA) was carried out as follows:

Bacteria were grown in 10 ml of nutrient broth (No. 2, (Oxoid)) overnight at 37° C. with continuous shaking at 120 rpm. The overnight cultures were diluted 1000× with iso-sensitest broth. The cultures were incubated at 37° C. with shaking for 1-2 hours to reach log CFU 6. Viability of the bacteria was estimated by colony forming unit (CFU) counts. From serial 10-fold dilutions of the experimental cultures, 100 μl samples were added to triplicate plates of nutrient agar plates (Oxoid) or blood agar plates (Oxoid). CFUs were counted after incubation of the plates at 37° C. for 24 hours.

Bacterial cultures: 10 μl of overnight cultures was added to 10 ml of fresh iso-sensitest broth to make the inoculation to $10^6$ CFU/ml. 290 μl of the cell suspension was added to each well of the 96 well plate, which was incubated at 37° C. for 24 hours. 300 μl of iso-sensitest broth without bacterial cells were added to wells of the plate as a no bacterial control.

MIC determination: The optical density of the bacterial cells was read at 405 nm using a plate reader (Bio TEK). The MIC concentration was determined as the lowest concentration of drug which inhibits the bacterial growth.

Compounds and Preparation

Mupirocin was dissolved in DMSO to the stock concentration of 10 mg/ml. HT00800059 was dissolved in $H_2O$ to the stock solution 30.07 mg/ml.

Mupirocin (10 mg/ml) was firstly diluted to 3.84 mg/ml, then further diluted in a serial of 2 fold dilutions. HT00800059 (30.7 mg/ml) was performed in a serial of 2 fold dilutions.

10 μl of each dilution from each drug was added to the 96 well plates in a two dimensional array as shown in the table below. This was followed by the addition of 280 μl of log phase culture at $10^6$ CFU/ml to make the final concentrations of each drug as shown in Table 1 and Table 2.

Combination of Mupirocin with HT00800059:

| 128 | 64 | 32 | 16 | 8 | 4 | 2 | 1 | 0.5 | 0.25 | 0.125 | 0 |
|---|---|---|---|---|---|---|---|---|---|---|---|
| 1024 | 1024 | 1024 | 1024 | 1024 | 1024 | 1024 | 1024 | 1024 | 1024 | 1024 | 1024 |
| 128 | 64 | 32 | 16 | 8 | 4 | 2 | 1 | 0.5 | 0.25 | 0.125 | 0 |
| 0 | 512 | 512 | 512 | 512 | 512 | 512 | 512 | 512 | 512 | 512 | 512 |
| 128 | 64 | 32 | 16 | 8 | 4 | 2 | 1 | 0.5 | 0.25 | 0.125 | 0 |
| 0 | 256 | 256 | 256 | 256 | 256 | 256 | 256 | 256 | 256 | 256 | 256 |
| 128 | 64 | 32 | 16 | 8 | 4 | 2 | 1 | 0.5 | 0.25 | 0.125 | 0 |
| 0 | 128 | 128 | 128 | 128 | 128 | 128 | 128 | 128 | 128 | 128 | 128 |
| 128 | 64 | 32 | 16 | 8 | 4 | 2 | 1 | 0.5 | 0.25 | 0.125 | 0 |
| 0 | 64 | 64 | 64 | 64 | 64 | 64 | 64 | 64 | 64 | 64 | 64 |
| 128 | 64 | 32 | 16 | 8 | 4 | 2 | 1 | 0.5 | 0.25 | 0.125 | 0 |
| 0 | 32 | 32 | 32 | 32 | 32 | 32 | 32 | 32 | 32 | 32 | 32 |
| 128 | 64 | 32 | 16 | 8 | 4 | 2 | 1 | 0.5 | 0.25 | 0.125 | 0 |
| 0 | 16 | 16 | 16 | 16 | 16 | 16 | 16 | 16 | 16 | 16 | 16 |
| 128 | 64 | 32 | 16 | 8 | 4 | 2 | 1 | 0.5 | 0.25 | 0.125 | 0 |
| 0 | 0 | 0 | 0 | 0 | 0 | 0 | 0 | 0 | 0 | 0 | 0 |

In the above table, values in bold text are for HT00800059. Values in plain text are for mupirocin. The numbers shown in each well are μg/ml.

Incubation of the compounds with the bacterial suspension was carried out for 24 hours. The kill effects of the drug combination were measured by optical density reading at 405 nm with a plate reader (Bio TEK).

The fractional inhibitory concentration (FIC) index was carried out as following: (MIC of drug A, tested in combination)/(MIC of drug A, tested alone)+(MIC of drug B, tested in combination)/(MIC of drug B, tested alone). The interaction was defined as synergistic if the FIC index was <1, additive if the FIC index was =1 and antagonistic if the FIC index was >1.

Results

Mupirocin Resistant Strain (28 Passages)

Chequerboard Analysis of Synergistic Effect Between Mupirocin and HT00800059 Against Mupirocin Resistant *S. aureus* (28 Passages)

| | | Mupirocin | | | | | | | | | | |
|---|---|---|---|---|---|---|---|---|---|---|---|---|
| | | 128 | 64 | 32 | 16 | 8 | 4 | 2 | 1 | 0.5 | 0.25 | 0.125 | 0 |
| HT00800059 | 1024 | 0.345 | 0.360 | 0.355 | 0.351 | 0.351 | 0.346 | 0.347 | 0.356 | 0.361 | 0.349 | 0.354 | 0.354 |
| | 512 | 0.344 | 0.347 | 0.353 | 0.348 | 0.348 | 0.346 | 0.347 | 0.352 | 0.350 | 0.350 | 0.355 | 0.360 |
| | 256 | 0.342 | 0.349 | 0.351 | 0.355 | 0.349 | 0.377 | 0.724 | 1.034 | 1.180 | 1.173 | 1.207 | 1.257 |
| | 128 | 0.345 | 0.352 | 0.352 | 0.365 | 0.498 | 0.830 | 1.099 | 1.162 | 1.173 | 1.183 | 1.216 | 1.242 |
| | 64 | 0.348 | 0.354 | 0.371 | 0.457 | 0.715 | 1.042 | 1.188 | 1.271 | 1.247 | 1.234 | 1.256 | 1.260 |
| | 32 | 0.347 | 0.358 | 0.399 | 0.523 | 0.816 | 1.054 | 1.164 | 1.210 | 1.264 | 1.238 | 1.296 | 1.310 |
| | 16 | 0.347 | 0.358 | 0.422 | 0.567 | 0.874 | 1.076 | 1.184 | 1.265 | 1.271 | 1.300 | 1.275 | 1.289 |
| | 0 | 0.346 | 0.363 | 0.480 | 0.726 | 0.968 | 1.136 | 1.208 | 1.244 | 1.252 | 1.246 | 1.255 | 1.337 |

Values in bold text represent growth. MIC: HT00800059 before combination was 512 and post combination was 64. Mupirocin before combination was 64 and post combination was 4. FIC: $64/512 + 4/64 = 0.375$.

Mupirocin Resistant Strain (24 Passages)

Chequerboard Analysis of Synergistic Effect Between Mupirocin and HT00800059 Against Mupirocin Resistant *S. aureus* (24 Passages)

|  | | Mupirocin | | | | | | | | | | |
|---|---|---|---|---|---|---|---|---|---|---|---|---|
|  |  | 128 | 64 | 21 | 16 | 8 | 4 | 2 | 1 | 0.5 | 0.25 | 0.125 | 0 |
| HT00800059 | 1024 | 0.367 | 0.359 | 0.362 | 0.360 | 0.354 | 0.355 | 0.352 | 0.354 | 0.351 | 0.351 | 0.347 | 0.351 |
|  | 512 | 0.368 | 0.353 | 0.353 | 0.356 | 0.347 | 0.349 | 0.346 | 0.345 | 0.343 | 0.346 | 0.343 | 0.344 |
|  | 256 | 0.349 | 0.349 | 0.350 | 0.349 | 0.345 | 0.350 | 0.379 | 0.384 | 0.518 | 0.652 | 0.678 | 0.809 |
|  | 128 | 0.354 | 0.348 | 0.354 | 0.357 | 0.352 | 0.478 | 0.675 | 0.857 | 0.936 | 0.851 | 1.002 | 1.025 |
|  | 64 | 0.347 | 0.347 | 0.351 | 0.357 | 0.392 | 0.627 | 0.844 | 1.015 | 1.011 | 1.023 | 1.038 | 1.086 |
|  | 32 | 0.368 | 0.353 | 0.353 | 0.368 | 0.426 | 0.669 | 0.921 | 1.061 | 1.029 | 1.002 | 1.098 | 1.354 |
|  | 16 | 0.349 | 0.349 | 0.352 | 0.378 | 0.443 | 0.679 | 0.964 | 1.063 | 1.068 | 1.075 | 1.109 | 1.375 |
|  | 0 | 0.358 | 0.356 | 0.359 | 0.386 | 0.454 | 0.629 | 0.863 | 1.056 | 1.109 | 1.083 | 1.170 | 1.368 |

Values in bold text represent growth. MIC: HT00800059 before combination was 512 and post combination was 64. Mupirocin before combination was 16 and post combination was 1. FIC: $64/512 + 1/16 = 0.1875$.

Conclusions

Resistant Strain 28 Passages
1. Mupriocin alone MIC 64 μg/ml.
2. HT00800059 alone MIC 512 μg/ml.
3. With mupirocin 32 μg/ml, HT00800059 MIC reduced to 64 μg/ml.
4. With HT00800059 at 256 μg/ml, mupirocin MIC reduced to 4 μg/ml.
5. There was a synergetic effect against mupirocin resistant strain with these two drugs as the FIC was 0.375.

Resistant Strain 24 Passages
6. Mupriocin alone MIC 16 μg/ml.
7. HT00800059 alone MIC 512 μg/ml.
8. With mupirocin 8 μg/ml, HT00800059 MIC reduced to 64 μg/ml.
9. With HT00800059 at 256 μg/ml, mupirocin MIC reduced to 1 μg/ml.
10. There was a synergetic effect against mupirocin resistant strain with these two drugs as the FIC was 0.1875.

The invention claimed is:

1. A pharmaceutical composition comprising dyclonine hydrochloride and 4-methyl-1-(2-phenylethyl)-8-phenoxy-2,3-dihydro-1 H-pyrrolo[3,2-c]-quinoline, wherein the combination of dyclonine hydrochloride and 4-methyl-1-(2-phenylethyl)-8-phenoxy-2,3-dihydro-1 H-pyrrolo[3,2-c]-quinoline shows a synergistic antimicrobial activity against log phase and/or latent microorganisms.

2. A pharmaceutical composition comprising dyclonine hydrochloride and 4-methyl-1-(2-phenylethyl)-8-phenoxy-2,3-dihydro-1 H-pyrrolo[3,2-c]-quinoline, wherein the combination of dyclonine hydrochloride and 4-methyl-1-(2-phenylethyl)-8-phenoxy-2,3-dihydro-1 H-pyrrolo[3,2-c]-quinoline shows a synergistic activity against stationary phase S. aureus.

3. A pharmaceutical composition comprising a combination of dyclonine or a pharmaceutically acceptable salt and/or solvate thereof, and 4-methyl-1-(2-phenylethyl)-8-phenoxy-2,3-dihydro-1 H-pyrrolo[3,2-c]-quinoline, or a pharmaceutically acceptable salt and/or solvate thereof, wherein the combination shows a synergistic antimicrobial activity against log phase and/or latent microorganisms.

4. A pharmaceutical composition comprising a combination of dyclonine or a pharmaceutically acceptable salt and/or solvate thereof, and 4-methyl-1-(2-phenylethyl)-8-phenoxy-2,3-dihydro-1 H-pyrrolo[3,2-c]-quinoline, or a pharmaceutically acceptable salt and/or solvate thereof, wherein the combination shows a synergistic activity against stationary phase S. aureus.

* * * * *